United States Patent [19]

Carson et al.

[11] Patent Number: 5,747,251
[45] Date of Patent: May 5, 1998

[54] POLYMERASE CHAIN REACTION ASSAYS TO DETERMINE THE PRESENCE AND CONCENTRATION OF A TARGET NUCLEIC ACID IN A SAMPLE

[75] Inventors: Dennis A. Carson, Del Mar; Hitoshi Kohsaka, San Diego, both of Calif.

[73] Assignee: The Regents of the University of California, Alameda, Calif.

[21] Appl. No.: 442,141

[22] Filed: May 16, 1995

Related U.S. Application Data

[63] Continuation of Ser. No. 354,449, Dec. 12, 1994, abandoned, which is a continuation of Ser. No. 88,077, Jul. 6, 1993, abandoned, which is a continuation-in-part of Ser. No. 958,291, Oct. 8, 1992, abandoned.

[51] Int. Cl.[6] ............... C12Q 1/68; C12Q 1/70; C12P 19/34; C07H 21/04
[52] U.S. Cl. ............... 435/6; 435/5; 435/91.2; 536/24.3; 536/24.32; 536/24.33
[58] Field of Search ............... 435/5, 6, 91, 2; 536/24.32, 24.33

[56] References Cited

U.S. PATENT DOCUMENTS 5,213,961  5/1993  Bunn et al. ............... 435/91.2
5,496,699  3/1996  Sorenson ............... 435/6

FOREIGN PATENT DOCUMENTS 9011374  10/1990  WIPO ............... 435/91.2

OTHER PUBLICATIONS

Friedhoff et al. Analytical Biochemistry 215:9–16, 1993.
Kwok et al. Genomics 13:935–941, 1992.
Nickerson et al.PNAS 87:8923–8927, 1990.
Sabbbatini Biotechniques 15: 706–713, 1993.
Quantitation of Plasma Human Immunodeficiency Virus Type 1 RNA by Competitive Polymearse Chain Reaction Scadden, et al., *The Jrnl. of Infect. Diseases*, 165:1119–1123, 1992.
Absolute quantification of target DNA: a simple competitive PCR for efficient analysis of multiple samples Zachar, et al., *Nucleic Acids Research* No. 8, 21:2017–2018, 1993.

Notice–13 Errata Scadden et al. *The Jrnl. of Infect. Diseases*, 167:195, 1993.
Solid–phase Polymerase Chain Reaction Kohsaka & Carson, Dept. of Medicine, The Sam & Rose Stein Institute for Research on Aging—UCSD, pp. 1–6+2 Figures, volume No. Not relevant.
Microtiter format gene quantification by covalent capture of competitive PCR . . . Kohsaka, et al., *Nucleic Acids Research*, No. 15, 21:3469–3472, 1993.
Delius et al. Nuc. Acids Res. 13(5): 5457–5469 (1985).
Syuängen et al., i bid., 16(23): 11327–11338 (1988).
Venetianer et al.PNAS, USA 71(10): 3892–3895 (Oct. 1974).

*Primary Examiner*—W. Gary Jones
*Assistant Examiner*—Dianne Rees
*Attorney, Agent, or Firm*—Fish & Richardson, P.C.

[57] ABSTRACT

Combinations of polymerization, non-competitive hybridization and assay techniques is disclosed. In one aspect of the method, one member of a regular or anchored primer pair is modified to include a coupling agent capable of forming a tight bond (resistant to uncoupling in an alkaline denaturing environment) with a reactant. Competitive PCR is performed and the PCR products are coupled via the coupling agent to a reactant on the surface of a solid phase support. The bond between the reactant and the solid phase support in this and all embodiments is also resistant to uncoupling in an alkaline denaturing environment. In another aspect of the method, a primer is tightly coupled to the bound reactant and a polymerization of the competitor and target nucleic acids is performed on the solid phase. A third embodiment uses at least three primers, one of which is internal to the PCR templates and is bound to the solid phase support on which the entire PCR takes place. In the first two embodiments, sense strands are completely removed from solution with the bound antisense strands of the PCR products. Hybridization with sequence-specific probes is then performed in the absence of competition for binding by the sense strands. Sense strand removal and hybridization is optional in the third embodiment, where the bound three-primer PCR products can be detected by a detectible signal. Quantification of the target template may preferably be achieved in all embodiments by an enzyme-linked immunosorbent assay (ELISA), using ELISA data analysis software and standard curves.

32 Claims, 10 Drawing Sheets

POLYMERASE CHAIN REACTION ASSAYS TO DETERMINE THE PRESENCE AND CONCENTRATION OF A TARGET NUCLEIC ACID IN A SAMPLE

This is a continuation of application Ser. No. 08/354,449, filed Dec. 12, 1994, now abandoned, which is a continuation of application Ser. No. 08/088,077 filed Jul. 6, 1993 now abandoned which is a continuation-in-part of Ser. No. 07/958,291 filed Oct. 8, 1992 now abandoned.

BACKGROUND OF THE INVENTION

1. Field of the Invention

This invention relates to detection and/or quantification of the amount of a target nucleic acid in a sample by a combination of polymerization techniques and an enzyme-linked immunosorbent assay (ELISA) performed on a solid phase support. In one aspect, the invention involves the use of polymerase chain reaction (PCR) technology, specifically an improved, quantitative method for performance of competitive PCR and determination of the concentration of a target nucleic acid in a sample. In another aspect, it relates to hybridization techniques which can be used to identify the relative ratios of target to competitor nucleic acids which have been amplified by the PCR. In the methods of the invention, either one strand of a double-stranded PCR product or a primer is captured onto a solid phase support by tight (preferably covalent) bonds which are resistant to uncoupling in an alkaline environment. The target to competitor ratio is then determined in the quantitative methods using appropriate hybridization detection means, preferably ELISA readers and related ELISA software. In another aspect of the invention, alleles of the target nucleic acid are characterized by identifying differences between the alleles in as little as one base pair.

2. History of the Prior Art

PCR is an in vitro method for the enzymatic synthesis of specific DNA or RNA sequences using oligonucleotide primers that hybridize to specific nucleic acid sequences and flank the region of interest in target nucleic acid. A repetitive series of cycles of template denaturation, primer annealing and enzymatic extension of the annealed primers results in an exponential accumulation of a specific nucleic acid fragment defined at its termini by the 5' ends of the primers. The resulting products (PCR products) synthesized in one cycle act as templates for the next; consequently, the number of target nucleic acid copies approximately doubles in every cycle.

The basic PCR techniques are described in U.S. Pat. No. 4,683,195 and 4,683,202 to Mullis, et al., the disclosures of which are incorporated herein. While these techniques have found widespread use in biology, their usefulness in clinical applications has been principally limited by three factors, to wit: (1) conventional PCR does not yield quantitative data it because the amount of nucleic acid increases exponentially and plateaus; (2) it will occasionally amplify non-specific nucleic acids, and (3) the PCR products must be assessed by semi-quantitative methods such as Southern blotting and densitometry. As a result, most PCR assays are limited to use in applications where the presence or absence of a specific, known nucleic acid molecule (usually DNA) is to be determined.

Recently, researchers have developed various methods intended to allow for quantification of PCR-amplified DNA or RNA. Generally, these approaches involve amplification followed by size analysis on agarose gels or DNA/RNA hybridizations followed by isotopic or enzymatic detection. For example, in *Proc. Ntl. Acad. Sci. USA*, (1992) 89:3241–3245, a method was reported involving heat (rather than alkaline) denaturation of the PCR product and hybridization in solution of the separated strands to two oligonucleotide probes. One probe is biotin labelled (a "capture" probe); the other is labelled with horseradish peroxidase (HRP) (a "detector" probe). Solution hybridization of the PCR product strands to the probes is performed in microtiter plate wells. These plate wells are coated with streptavidin hydrophobically bound thereto which is intended to bind with the biotinylated probe. After washing, an HRP chromogen is added to the wells, absorbance is measured by a microtiter plate reader and ratios of PCR product separately bound by the probes are measured against a standard curve.

A material drawback of this approach is that the PCR strands must be separated by denaturation prior to their addition to the microtiter plate wells because the hydrophobic bonds between the streptavidin and the wells can be destroyed by heating. As a result, the separated strands can rehybridize in solution, thus competing with the probes and compromising the reliability of the method. Further, the reagents used in the method must be added immediately to the plate wells with the PCR products or the reaction cannot be completed. The method also lacks an internal amplification standard such as would be provided by use of a competitor nucleic acid template during the PCR phase of the analysis.

The technique for providing an internal amplification standard using a competitor template which differs principally in size from the target is described in *Proc. Natl. Acad. Sci. USA*, (1990) 87:2725–2729. The target and competitor templates differ by the presence of a relatively large (about 100 base pair) naturally-occurring intron in the competitor template. Coamplification of target and competitor templates by the PCR occurs in solution; size differences between the polymerization products are identified by electrophoresis. Alternatively, the competitor template can differ from the target by the presence or absence of a restriction site. The templates are then distinguished on the basis of size by restriction enzyme digestion following PCR.

This method, however, has several drawbacks. In the electrophoresis approach, the magnitude of the size difference between the competitor and target must be relatively large to allow for their distinction on the basis of size alone. This size differential enhances the possibility that the amplification efficiencies of the templates will differ substantially, thus skewing the end measurement of the target template. The accuracy of the restriction enzyme approach is also limited by how precisely the restriction fragments are separated. Neither method is susceptible to automation.

Another approach uses a competitor nucleic acid sequence into which a lac operator sequence is introduced by in vitro mutagenesis. As described in *Biotechniques* (1991) 10:68–75, the PCR products are immobilized on magnetic beads using biotin-streptavidin bonds. A ratio between target DNA and the mutated DNA is determined using a fusion protein (*E coli*. Lac I repressor fused to β-galactosidase) which binds to the lac operator sequence and a colorimetric detection method. The relatively large size of the lac operator sequence (21 base pairs) limits the efficiency of the PCR in this method, as does the need for complete binding of the fusion protein. In particular, even minor differences in amplification efficiencies between the target and mutated DNA would be significant, because those differences are magnified in each successive PCR cycle.

Another approach is reported in *J. Clin. Invest.* (1991) 88:1755–1759. A noncompetitive PCR is performed in this method following by hybridization to an immobilized biotinylated probe and an unbound HRP-labeled probe. The biotinylated probe is bound to avidin-coated microtiter plate wells. However, because the avidin is hydrophobically bound to the wells, no denaturation of the PCR products is performed. As a result, one strand of the PCR products compete with the probes for binding to the other strands, thus limiting probe hybridization.

The same limitation is present in a method for identifying particular mutations or polymorphisms in genes described in Saiki, et al., *Proc. Natl'. Acad. Sci., U.S.A.*, 86:6230–6234, 1989. The described method covalently links oligonucleotide probes to separate nylon membranes for each probe using UV irradiation. Target double-stranded DNA samples are then hybridized to the immobilized probes and the hybrids detected by a colorimetric reaction.

However, because the sense strands of the PCR products are not removed from solution prior to hybridization, their renaturation with the antisense strands limits probe hybridization. The method described could not be adapted to remove the competing strand because it is the hybridization probe, not the PCR primers or products, which are immobilized. Also, as described, is not quantitative and requires the use of multiple and separate nylon membranes.

It is clear, therefore, that a need for an efficient, simple, method for determining the quantity of a target nucleic acid in a sample still exists, particularly for use in diagnostic applications. It is also clear that a need exists for a method whose precision is not limited by competition for binding of the hybridization probes to the target and competitor nucleic acid templates. These needs are addressed by the methods disclosed herein.

SUMMARY OF THE INVENTION

1. Definitions.

The following definitions are provided to simplify discussion of the invention. Those skilled in the art, however, will recognize that these definitions may be expanded to include equivalents without departing from the legitimate scope of the invention. For this reason, these definitions should not be construed as limiting the invention.

a. "Tight bond" or "tightly bound" means a chemical bond which is highly resistant to uncoupling under denaturing conditions (as provided, for example, in a 0.1N NaOH solution). Preferably, this bond will be a covalent one between coupling agents and reactants identified infra.

b. "PCR" refers to the polymerase chain reaction protocols which are known in the art and used to amplify nucleic acids.

c. "Template strands" refer to strands of nucleic acids which are used to produce complementary strands of nucleic acid in polymerization protocols, including PCR. For convenience, these strands will be referred to as antisense or bound strands when to the solid phase, although it will be understood that sense strands may instead be the bound strands of the PCR product.

d. "PCR products" refers to template and complementary strands of nucleic acids amplified by the polymerase chain reaction.

e. "Polymerization product" refers to template and complementary strands of nucleic acids produced by polymerization not involving a chain reaction.

f. "Denaturing conditions" refers to those conditions under which bonds between strands of a nucleic acid will uncouple. More particularly, it refers to the environment (preferably an alkaline one) which must be present to completely remove unbound complementary strands of nucleic acids from solution in the methods taught herein.

g. "Solid phase support" refers to a solid material on which hybridization can be performed. In certain embodiments of the invention, the solid phase support must also be formed of a material on which polymerization may be performed. Where the polymerization is performed by the PCR, this material must be stable to the high temperatures used in the reaction. Examples of suitable materials and structures for use as solid phase supports are described infra.

h. "Competitor" refers (depending on context) to a competitor nucleic acid template or complementary nucleic acid produced from the competitor template according to the methods of the invention.

i. "Target" refers (depending on context) to a wild-type nucleic acid template or complementary nucleic acid produced from the wild-type template according to the methods of the invention.

j. "Standard curve" refers to a graph of datapoints from which the concentration of a target nucleic acid may be calculated.

k. "Detection tag" refers to a label capable of producing a detectible signal indicative of the presence of the nucleic acids of interest in an assay sample. It may comprise a radioisotope, a nucleotide chromophore, a fluorescent molecule, a chemiluminescent molecule, a bioluminescent molecule or a colloidal metal, but will preferably be an enzyme or substrate which is reactive with an enzyme. It may also comprise an antigen which will be specifically bound by an antibody to which a detection tag is attached.

l. "Assay Sample" refers to any sample in or converted to solution which is suspected of containing the target nucleic acid.

m. "Hybridization primer" refers to a primer which will hybridize to a nucleic acid(s) which has been polymerized by a primer pair in solution (i.e., a PCR product). In the context of the invention, hybridization primers are tightly bound to a solid phase support.

2. Discussion.

The invention consists in one aspect of (a) a novel combination of competitive PCR, (b) hybridization of single strands of the PCR products with sequence-specific probes (SSO's) on a solid phase support (such as ELISA microtiter plate wells, (hereinafter "ELISA plate wells"), (c) performance of an appropriate assay, and (d) calculation of the ratio of competitor nucleic acid to target nucleic acid by comparison to a standard curve (preferably by using ELISA data analysis software).

Specifically, this embodiment of the invention, competitive PCR is performed using a competitor template containing an induced mutation of one or more base pairs which results in the competitor differing in sequence (but not size) from the target template. One of the primers is biotinylated or, preferably, aminated so that one strand (usually the antisense strand) of the resulting PCR product can be immobilized via an amino-carboxyl, amino-amino, biotin-streptavidin or other suitably tight bond to a solid phase support which has been tightly bound to an appropriate reactant. Most preferably, the bonds between the PCR product, solid phase support and reactant will be covalent ones, thus reliably rendering the bonds resistant to uncoupling under denaturing conditions. Once the aminated or biotinylated strands of the PCR products are immobilized, the unbound complementary strands are separated in an alkaline denaturing wash and removed from the reaction environment. For simplicity, the bound strand will be referred to hereafter as binding or antisense strands and the unbound strands will be referred to as sense or complementary strands.

SSO's corresponding to the target and competitor nucleic adds are labelled with a detection tag. The SSO's are then hybridized to the antisense strands in absence of competition from the removed unbound sense strands. Appropriate assay reagents are added and the degree of hybridization is measured by ELISA measurement means appropriate to the detection tag and solid phase support means used, preferably an ELISA microplate reader. The measured values are compared to derive target nucleic acid content, using a standard curve separately derived from PCR reactions amplifying templates including target and competitor templates.

This method is advantageous in that it is quantitative, does not depend upon the number of PCR cycles, and is not influenced by competition between the SSO probe and the complementary strand in the PCR product. The latter feature in particular is an advance made possible by the use of tight bonds between the reactant and the solid phase support and between the reactant and a coupling agent on the antisense strands, allowing for immobilization of the antisense strands and complete removal of sense strands. It will be appreciated that the precision of this method is greatly improved over the prior art methods described supra because, in absence of competition for binding, the SSO's can distinguish very small mutations in the competitor nucleic acid (i.e., in as little as 1 base pair). Further, because the method does not require that the target and competitor templates differ in size, the probability that the amplification efficiencies of the target and competitor templates will be equivalent is greatly enhanced, which in turn greatly enhances the accuracy of the target template measurement. Further, the quantifying steps of the method can be automated and easily performed using existing ELISA equipment widely used in clinical laboratories.

In another aspect of the invention, part of the polymerization step and all of the hybridization step are performed on a solid phase support. In this embodiment, it is an nucleotide polymerization primer (preferably an oligonucleotide) which is captured onto a solid phase support rather than a strand of the PCR products. Target and competitor nucleic acid PCR products are then added in solution to the solid phase support and a polymerization step is performed. The unbound sense strands of the polymerization product are removed under the denaturing conditions described above. A target to competitor nucleic acid ratio can be determined by detection of labelled oligonucleotide SSO probes using appropriate measurement means (preferably ELISA readers) and standard curve as described supra. The efficiency of this method can be so great that a chain reaction in the polymerization step may be unnecessary, thus shortening the time needed to perform the method. The accuracy of the method is also enhanced because the final polymerization products do not have to be transferred from a reaction tube to a solid phase support for hybridization, thus limiting the potential for their loss or damage. If necessary for a particular sample, however, the PCR may be used to amplify the target and competitor nucleic acids in a separate reaction tube, followed by a final polymerization performed on the solid phase support.

In yet another aspect of the invention, the polymerization step is performed in a single step on a solid phase support. In this embodiment, the PCR is performed to amplify the target (and where a quantitative analysis is desired, the competitor) nucleic acid on a solid phase support. Before the PCR is performed, primers (which correspond to the target and competitor nucleic acids) are tightly bound to the solid phase support. Two additional primers are placed into solution with the target nucleic acid (or three primers where a competitive template is present). These primers will be conventional ones selected as described infra.

As the PCR begins, the templates do not interact with the bound primer to a substantial degree because template concentration is relatively low and the bound primer is not readily accessible. However, as the templates are amplified, more of the PCR products become bound to the solid phase via hybridization with the bound primer. In essence, therefore, the bound primers serve as hybridization probes for the PCR products formed by priming of the target and competitor nucleic acids. Once hybridization occurs, the hybridization primer elongates via the PCR.

Molecules capable of providing different, detectible signals indicative of the formation of bound PCR products known to those skilled in the art (such as labelled nucleotide chromophores which will form different colors indicative of the formation of target and competitor PCR products) can be added to the reaction solution during the last few cycles of the reaction. The ratio between the target and competitor nucleic acids can also be determined by ELISA or other appropriate measurement means and reagents reactive with detection tags coupled to the 3' end of the immobilized hybridization primers. This method may also be adapted to detect whether a particular gene is present in the sample (without quantifying it) by performing a conventional noncompetitive PCR protocol.

The methods of the invention therefore provide means of detecting or, preferably quantifying the amount of a target gene present in a sample which vary in accuracy and simplicity of the PCR products. Because either a strand of the PCR product or the primers are tightly bound to a solid phase in the polymerization/hybridization methods, complete removal of the unbound complementary strands and elimination of competition by it with the SSO's is possible. As a result, these methods are highly accurate and relatively simple to perform as compared to prior art PCR assay procedures.

The most simple method is, of course, the one-step, solid phase, multiple primer polymerization. Although this method may not be as accurate as the other methods of the invention, it can be of value where the benefits of simplicity outweigh the need for complete accuracy. For example, this method could be used for performing relatively routine diagnostic evaluations in a hospital laboratory.

It will be appreciated, however, that all of the methods of the invention are as, if not more accurate, than prior art PCR assay techniques, particularly competitive PCR techniques. When used to quantify the target nucleic acid in a sample, this is because the methods do not require that the target and competitor templates differ in length or by the presence of internal restriction sites. Instead, the target and competitor templates used in the described methods can differ in sequence (but not in length) by as little as one base pair. As a result, the amplification efficiencies of the target and competitor templates are closer to the ideal of a 1:1 ratio than other known competitive PCR protocols. In addition, even when used on a nonquantitative basis, immobilization of the PCR product or primers and removal of sense strands permits detection of mutations or polymorphisms among nucleic acids in the sample of as little as one base pair.

DETAILED DESCRIPTION OF THE PREFERRED EMBODIMENTS

Figure 1:
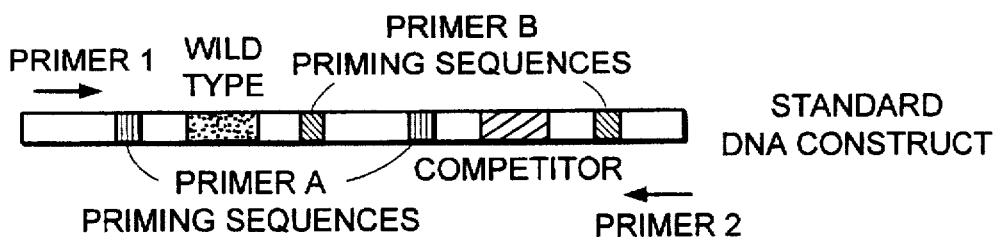
FIG. 1 is a diagrammatic and representative depiction of a standard DNA construct used in the present method.

Throughout this description, the preferred embodiment and examples shown should be considered as exemplars, rather than limitations on the present invention.

Two known polymerization protocols, as modified in the manner described herein, provide the foundation for performance of the improved protocols claimed. The first protocol is conventional PCR first described in U.S. Pat. Nos. 4,683,195 and 4,683,202. The second may be used in all of the embodiments described herein and is known as competitive PCR. Competitive PCR is fundamentally described by Gilliland, et al., in *Proc. Natl. Acad. Sci. USA* (1990) 87:2725–2729, the disclosure of which is incorporated herein by this reference. In summary, competitive PCR (as described by Gilliland) comprises the generation of target and competitor templates, the latter of which contains either a naturally occurring intron of up to 100 base pairs or a base pair substitution prepared by site-directed mutagenesis using PCR, resulting in a competitor template which differs in length from the target sequence. As a result, amplification of each is expected to proceed in a substantially similar manner.

In the Gilliland, et al., method, the PCR products (target or competitor) are distinguished on the basis of size by gel electrophoresis. Neither the size difference nor the electrophoresis step are required in the improved methods described below.

Where the 5' terminus of the target sequence is not known, a second protocol (anchored PCR) can be performed in conjunction with the improved competitive PCR method described herein. The anchored PCR method utilizes a specific, known 3' primer and another primer to which an "anchor" is attached (which anchor usually consists of a poly (dG) or (dA) tail having convenient restriction sites). The method for performance of anchored PCR is described in detail by Loh, et al., in *Science* (1989) 243:217–220, the disclosure of which is incorporated herein by this reference. Other protocols (such as inverse and nested PCR) known to those skilled in the art may also be appropriate for use in particular applications if performed in conjunction with the competitive solid phase polymerization techniques taught herein.

For further background, those skilled in the art may wish to refer to Innis, et al., "Optimization of PCR's", *PCR Protocols: A Guide to Methods and Applications* (Acad. Press, 1990). This publication describes parameters which can be used to influence the specificity, fidelity and yield of the desired PCR products.

It will be understood by those skilled in the art that several known, quantitative assay procedures could be employed to deduce the ratios of target and competitor nucleic acids present in the assay sample, including immunoassay, radioimmunoassay and colorimetry. However, because of the wide availability of ELISA equipment in clinical and research laboratories, and the suitability of ELISA plate wells for use as the solid phase support in the methods of the invention, use of the ELISA procedure is preferred.

Reactants, coupling agents and detection tags which are suitable and/or preferred for use in all methods of the invention are identified in Example I below. Suitable and preferred solid phase supports for use in all methods of the invention are also identified in Example I, although microtiter plate wells are the preferred solid phase support. Kits suitable for use in performing the methods of the invention including such reagents and solid phase supports are also within the scope of this invention.

Possible applications of this invention include, but are not necessarily limited to:

(1) Diagnosis and typing of infectious diseases such as HIV, venereal disease, hepatitis, mycobacterial infections, etc.;

(2) HLA typing for organ transplantation and autoimmune disease diagnosis;

(3) Cancer diagnosis through oncogene detection;

(4) Diagnosis of genetic diseases;

(5) Monitoring of inflammatory diseases by assessing quantitative cytokine gene expression.

Examples of several of these applications are provided below. The method is of particular value for use in polymorphic gene detection because it can detect very small differences in nucleotide sequences between alleles and can quantify the number of alleles present in a sample. However, those skilled in the art will appreciate that as an analytical tool, the methods described below may be of use in applications other than those suggested above.

The first example below generally describes how the method of the invention where the PCR products are immobilized after polymerization is to be performed. Specific illustrations of how this method can be applied to (1) determine the frequency of expression of T cell receptor variable region genes in human patients with rheumatoid arthritis and (2) determine the quantity of envelope gene for the human immunodeficiency virus in a sample are provided at Examples II through IV.

An alternative method wherein the final polymerization step and the hybridization step are both performed on the solid phase support is described in Example V in the context of quantifying the HIV envelope gene in a sample.

Another alternative method wherein the entire polymerization step (and, optionally, the hybridization step) are performed on the solid phase support is described generally in a stepwise fashion in Example VI. It will be understood that each method described in Examples I, V and VI can be used in any appropriate application, including the tissue typing, HIV envelope gene quantification and TCR expression determination applications illustrated in Examples II through IV.

Examples VII through XI provide descriptions of solid phase supports and means for coupling the PCR products and/or primers to the solid phase support which may be used as alternatives to those described in the preceding examples. Again, it will be appreciated that the examples are provided as illustrations; equivalent supports and means for coupling may be apparent to those skilled in the art and are within the spirit and scope of this invention. In addition, use of equivalent coupling agents, reactants, detection tags, reagents and polymerization protocols in the steps disclosed are considered to be within the scope of this invention.

EXAMPLE I

QUANTITATIVE GENE ANALYSIS USING PCR PRODUCTS TIGHTLY BOUND TO A SOLID PHASE SUPPORT

A. Preparation of Materials For Use in Amplification and Hybridization

1. Preparation of competitor nucleic acid templates.

A first step preparatory to performing the method is to prepare a competitor nucleic acid template generally according to the technique taught by Gilliland, et al., supra with the modification that the competitor nucleic acid will differ in sequence (by at least 1 base pair) but not length from the competitor. It will be appreciated by those skilled in the art that this technique and the methods described herein can be applied to RNA and DNA, whether double or single-stranded. Appropriate modifications of the PCR protocol for use with either RNA, DNA or both are taught in U.S. Pat. Nos. 4,603,195 and 4,603,202 and are known to those skilled in the art. Most commonly, the nucleic acids used in the methods of the invention will be double-stranded DNA. It will be understood, however, that the method is not so limited and may be used with single-stranded DNA or RNA.

In a preferred embodiment of the invention, the competitor nucleic acid will be prepared by site-directed mutagenesis of at least 1 base pair. This approach enhances the amplification efficiency of the competitor so that it can be expected to be coamplified in substantially a 1:1 ratio with the target template. It also simplifies collection of starting materials in that any gene can be used.

2. Preparation of reactant-coated solid phase support means.

The solid phase support (here, ELISA plate wells) is also prepared for use in the method by coating of the support with an appropriate coupling reactant. The material used for the solid phase support can also have the coupling reactant incorporated into its surface. The principal characteristics of the chosen reactant will be its ability to form a covalent bond with the support and to form a tight bond, and preferably a covalent one, with the coupling agents on the antisense strands of the PCR products. For this reason, plastics are preferred materials for use in the solid phase support, with polystyrene, polyvinyl chloride and polycarbonate plastics being most preferred. Some examples of suitable plastics can be found in Place, et al., *J. Immunol Methods*, 48:251–260, 1982; and Gronowitz, et al., *Biotech. and Applied Biochem.*, 13:127–142, 1991. In this embodiment, binding of the antisense strands is made possible by use of an oligonucleotide primer in the PCR which has been modified to include a coupling agent corresponding to the reactant coating of the solid phase support.

This tight bond must resist being uncoupled under denaturing conditions (here, a 0.1N alkaline wash) to ensure immobilization of antisense strands throughout the process. For this reason, covalent coupling agent to reactant bonds are preferred, although biotin-avidin bonds are sufficiently tight for use in the invention if the avidin is covalently, rather than hydrophobically, bound to the solid phase support.

The reactants identified herein possess these characteristics and are resistant to being washed away from the wells during the denaturing step of the method; other equivalent reactants may suggest themselves to those skilled in the art, but the reactants listed herein are considered to be preferred ones.

It is expected that the choice between these reactants in a particular application (and its corresponding binding molecule for attachment to one of the primers) will be principally be dictated by manufacturing costs. Appropriate reactants, coupling agents and binding reactions are:

| Reactant Coating for Solid Phase Support Means | Corresponding Coupling Agent and Binding Reaction |
|---|---|
| Amino group | Amino group or carboxyl group (to form amine-amine bonds and amino-carboxyl bonds) |
| Carboxyl group | Amino group (to form amino-carboxyl bonds) |
| Cysteamine | Mercaptoethanol (to form disulfide bonds) |
| Streptavidin (covalently, not hydrophobically bound) | Biotin (to form a biotin-streptavidin bond) |

Covalently coated aminated and carboxylated plates are commercially available from Costar of Cambridge, Mass.

All bonds known in peptide chemistry are expected to be suitable for use in forming amino-amino or amino-carboxyl bonds. Suitable coupling reagents (e.g., hetero- and homo-bifunctional cross-linkers) are available through Pierce Chemical, Rockford, Ill. (see, e.g., its 1993 Immunotechnology Products Catalog).

It should be understood that while use of microtiter plate wells as the solid phase for immobilization of one strand of the PCR product is preferred (to permit use of conventional plate readers as the hybridization detection means), the method is not necessarily so limited. Other solid phase supports such as fibers or beads formed of any biologically compatible material known in the art (such as glass or plastic) may be suitable.

Use of fibers, beads and similar solid phase supports provides a greater surface area for attachment of oligonucleotide primers or PCR products and may, therefore, enhance the accuracy of the assay. To enable the use of conventional ELISA equipment, however, the beads or fibers should be suspended in solution in ELISA plate wells.

3. Selection and modification of primer pairs.

Once the competitor templates are prepared, appropriate primer pairs are selected for coamplification of the target and competitor sequences. Criteria and means for selection of appropriate primers for competitive PCR and means for their preparation are well-known in the art and will not, therefore, be described in detail here. For reference, however, Innis, et al., "Optimization of PCR's", supra, has a concise discussion of how to select and prepare primers for PCR.

To enable one strand of the PCR product to be tightly bound to the solid phase support, one of the primer pairs was modified at its 5' end to include a coupling agent appropriate for reaction with the corresponding reactant coating the solid phase. For example, as suggested above, where microtiter plate wells are carboxylated, the modified primer pair will include an amino group as the coupling agent at its 5' end. In this example, the coupling agent was a carboxyl group. Modification of the primer can be conveniently performed by introducing the coupling agent during synthesis of the primer using an automated oligonucleotide synthesizer, such as the commercially available DNA synthesizer from Applied Biosystems of Foster City, Calif.

4. Synthesis of sequence-specific hybridization probes and attachment of hybridization detection tag.

Appropriate sequence-specific hybridization probes are synthesized, one of which was complementary to the target nucleic acid and the other of which is complementary to the specific mutation sequence in the competitor nucleic acid. The probes are labelled with an enzymatic, antigenic, fluorescent, chemiluminescent, bioluminescent, or colloidal metal hybridization detection tag according to means known in the art (with the qualification that the detection tag must not be complementary to the reactant coating the solid phase). For example, if the solid phase was coated with streptavidin, biotin should not be used as the hybridization detection tag on the probes to avoid attachment of the probe to the solid phase. Also, as noted previously, use of an enzyme as the detection tag or as a reagent for a suitable substrate used as the detection tag is preferred to allow use of ELISA procedures. Among the kinds of detection tags suggested, those skilled in the art will be able to select suitable tags which are capable of providing a detectible signal indicative of the formation of PCR product/probe hybrids or, in the case of the one-step method, of PCR products, without undue experimentation. Equivalent tags to those used in these Examples will not, therefore, be described in detail here.

5. Attachment of an anchor.

Where the sequence of the target DNA is not known, modification of the primer, target and competitor nucleic acids to include anchor and anchor hybridization sequences will also be performed substantially according to methods which are well-known in the art, such as those taught in *Science*, supra at 243:217–220.

B. Performance of Method

Conventional or anchored PCR is performed to coamplify the target and competitor templates using the modified and unmodified primers. The PCR products may be purified by minicolumn (using, for example, the MAGIC PCR PREPS product from Promega of Madison, Wis.). The resulting products will consist of antisense strands having the coupling agent attached thereto and sense strands without coupling agent.

Immobilization or capture of antisense strands is performed by placing a diluted aliquot of the double-stranded PCR products onto the solid phase support (here, coated ELISA plate wells). The PCR products are allowed to stand in the plate wells in the presence of a coupling reagent for a period of time sufficient for capture of the antisense strands bearing the coupling agent to the reagent coating each well. Sense strands are then separated from the captured antisense strands and removed from the solution in each plate well by incubation with an alkaline denaturing salt (such as 0.1N NaOH) and washing with a buffer solution.

After removal of the unbound sense strands, the labelled probes are added to each plate well and hybridization is allowed to occur with the captured antisense strands. A substrate, antibody or other assay reagent appropriate to interact with the label used on the probes is added to each plate well and the reaction stopped at an appropriate point. An ELISA microplate reader (such as the THERMO MAX microplate reader from Molecular Devices of Menlo Park, Calif.) is used to measure absorbance in each well and the values compared to a standard curve to derive input DNA content as described further below.

If a chemiluminescent hybridization detection tag is used and a reagent, such as an alkaline phosphatase substrate, is added to react with the detection tag, emitted photons will be measured instead of OD. This approach enhances the linear range of the measurements in that it avoids the loss of sensitivity in OD measurements experienced at high OD values. A suitable microplate reader for use with a chemiluminescent tag is commercially available from Dynatech of Chantilly, Va.

Where a fluorescent tag is used, a suitable ELISA microplate reader is commercially available from Millipore of Boston, Mass.

C. Generation of Standard Curves for Calculation of the Ratio of Target to Competitor Nucleic Acid Probe hybridization-based quantification of PCR products can eliminate false positive results derived from non-specific amplification. However, potential flaws can come from differences in hybridization or labeling efficiency of the probes. The standard construct used for this example has tandemly arranged wild type DNA and competitor DNA sequences. Since the standard curves were generated from the results of hybridization of each probe with the standard construct, labeling or hybridization efficiency did not affect the results.

A nucleic acid standard (hereafter referred to for convenience as "standard DNA" construct) is constructed according to means known in the art to include two tandemly aligned DNA regions from wild type (target) DNA and competitor DNA. A suitable standard DNA construct is diagrammatically depicted in FIG. 1. Conventional PCR is performed to amplify the standard DNA using a reactant modified primer (such as an aminated primer) and a regular primer. Two sets of serial dilutions of the standard DNA PCR products were prepared.

Separately, samples containing target DNA to which competitor DNA was added in known quantity were coamplified according to the method described in paragraph B of this Example. Two aliquots of the PCR products were made; both aliquots were added to microtiter plate wells for covalent coupling of antisense strands and removal of sense strands as described supra.

Figure 2:
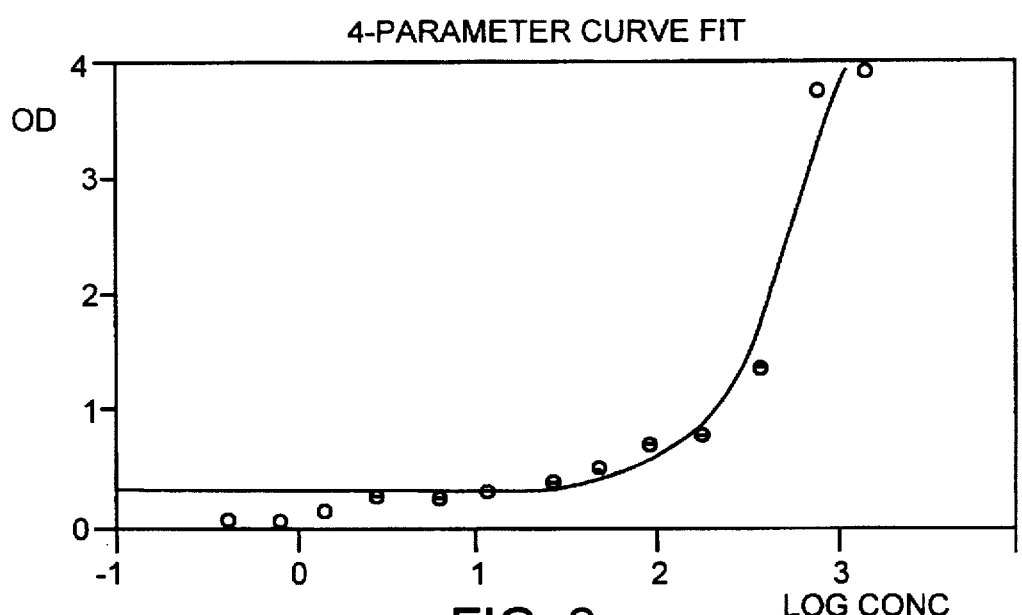
FIG. 2 graphically depicts a sample standard curve that relates the known concentration of a target nucleic acid in a sample to optical density as measured by an ELISA plate reader.
Figure 3:
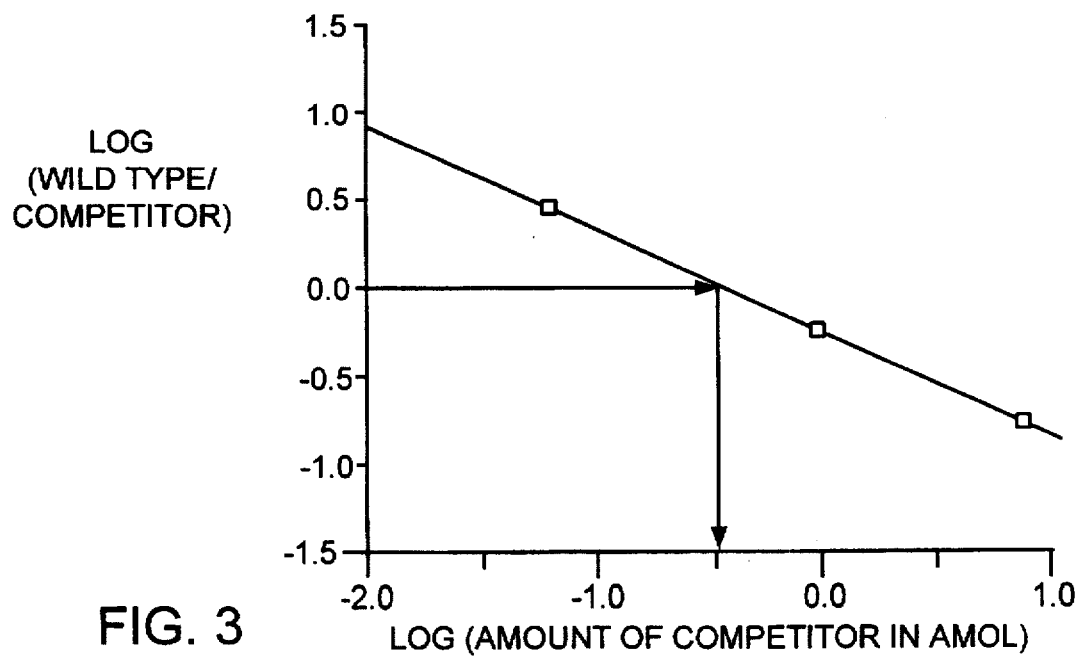
FIG. 3 graphically depicts a plot of the log of the ratio of the concentration of a target nucleic acid to a competitor nucleic acid determined using the embodiment of the invention wherein one strand of the PCR products are tightly bound to ELISA plate wells.

Hybridization was performed separately with the two sets of standard DNA solutions and the two sample/competitor DNA aliquots. The SSO's used corresponded to the target sequence and the competitor sequence. After hybridization, an assay appropriate to the detection tag used was performed and optical density or another appropriate value was measured with appropriate hybridization detection means as described supra.

Where the SSO's are not known to have equal hybridization efficiencies, a separate standard curve is generated for each SSO based on the adsorbence (OD) readings provided by use of the microtiter plate reader. (Only one curve is needed where no differences in the hybridization efficiencies for each probe is expected). A representative standard curve plotting OD against the logarithmic concentration of each probe is shown in FIG. 2. ELISA data analysis software (such as the DELTA SOFT version 2.1 sold by BioMetallics of Princeton, N.J.) is then used to calculate the amount of target DNA in the sample. Using this data, a ratio of target to competitor products can be calculated.

Where the approximate amount of target DNA present in the sample is not known, target DNA samples can be mixed with various known concentrations (usually three) of competitor DNA. Competitive PCR is then performed according to the methods described herein and the ratio of target DNA to competitor calculated. A graph is then generated as depicted in FIG. 3 which plots the known concentrations of competitor against the ratios of target and competitor sequences determined by covalent capture PCR in logarithmic scales. Calculation of the amount of competitor which would give a 1:1 ratio will provide the approximate concentration of target DNA in the starting samples.

EXAMPLE II

DNA POLYMERIZATION AND HYBRIDIZATION TO QUANTIFY HUMAN IMMUNODEFICIENCY VIRUS I ENVELOPE (HIV-1 env) GENE IN A BIOLOGICAL SAMPLE (USING THE METHOD OF EXAMPLE I)

In this example, the inventive method (here, the embodiment described in Example I) was used to determine the quantity of a human immunodeficiency virus envelope gene (HIV-1 env) in a population of infected cells.

A. RNA Extraction and Reverse Transcription

Total RNA was isolated from $3 \times 10^5$ CEM cells infected with HIV-1 using RNA STAT-60 (Tel Test B), as described in Ravza, et al., *J. Virol.* (1989) 63:3700–3707. It was reverse transcribed with SUPERSCRIPT II reverse transcriptase (Life Technologies, Gaithersburg, Pa.) and a HIV-1 env gene specific primer 88–272, as described in Davis, et al., *J. Infect Dis.* (1990) 162:13–20.

B. Construction of Competitor DNA and Standard DNA

A short fragment of the HIV-1 env gene was amplified with two gene specific primers, 88–79 and 88–272, as described in Davis, et al, *J. Infect. Dis.*, supra. The amplification mixture contained 100 µl of 20 mM Tris-HCl (pH 8.2), 10 mM KCl, 2 mM $MgCl_2$, 6 mM $(NH_4)_2SO_4$, 0.1% TritonX-100, 10 ng/µl BSA, 200 µM dNTPs and 2.5 u Pfu DNA polymerase from Stratagene (of La Jolla, Calif.). The primers were at a concentration of 1 µM. The amplification included 30 cycles of 95° C. for 30 seconds, 42° C. for 30 seconds and 72° C. for 1 minute followed by final extension for 7 minutes. PCR products were subcloned into pBluescript II SK+ (Stratagene), and termed pENVwt (where "wt"=wild type). In order to generate a mutant env gene fragment, pENVwt was reamplified either with 88–79 and HE1 primer (5'-CGC CAT TTG ACC ATT CAT TTG TAC ATG GTC) (SEQ ID No:1) or with 88–272 and HE2 primer (5'-AAT GGT CAA ATG GCG TTA CAC ATG GAA TTA G) (SEQ ID No:2) (see, FIGS. 4 (*a*) and (*b*) for a complete description of these 4 primers). Each product was purified to remove free primers with MAGIC PCR PREPS minicolumns (from Promega of Madison, Wis.) and the mixture was reamplified with 88–79 and 88–272. The resulting mutant gene fragments were subcloned into the same vector and termed pENVcomp (where "comp"=competitor). The cloned mutant env gene fragment was the same length as the gene fragment contained in the PENVwt vector.

Figure 4:
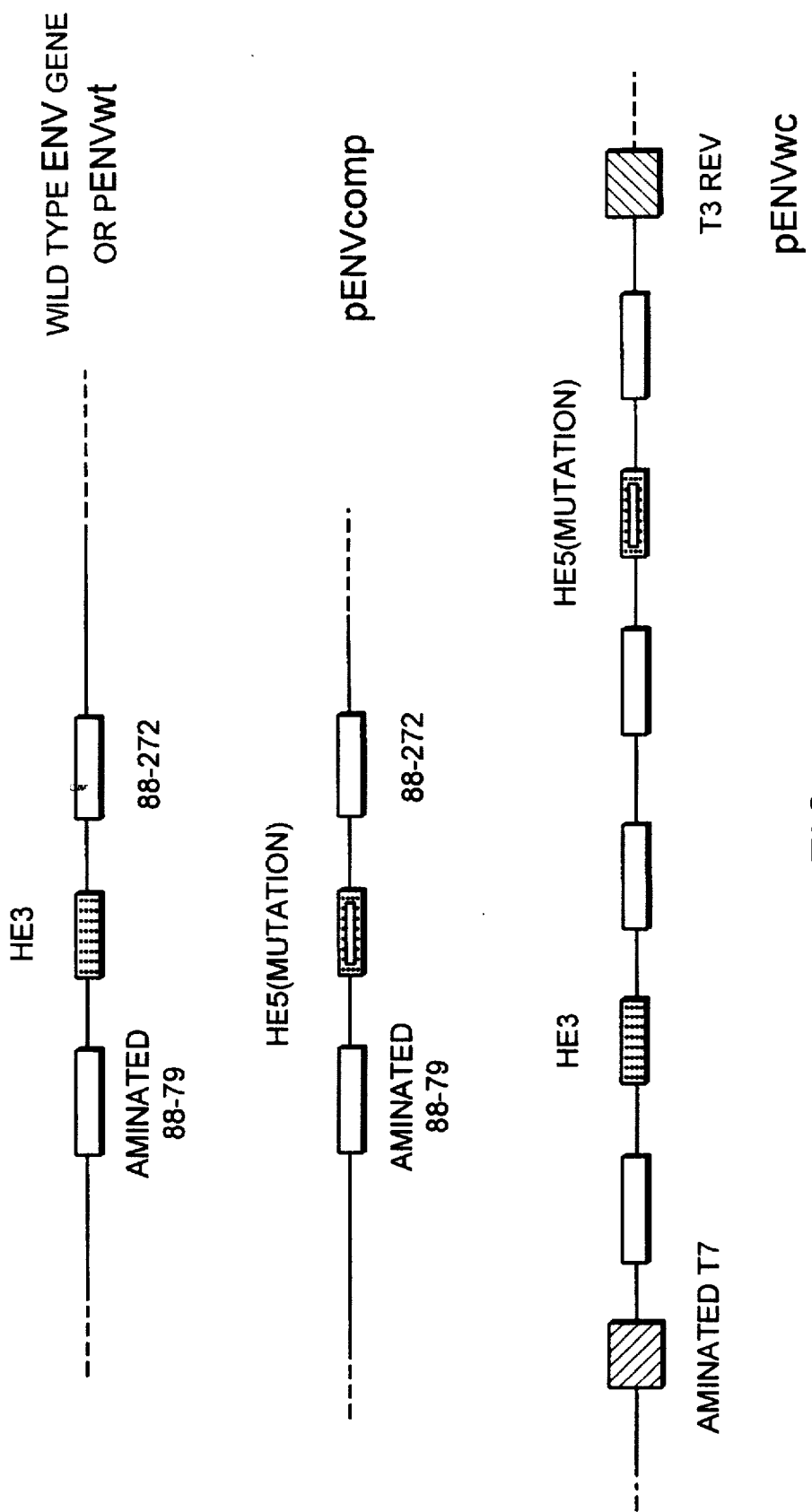
FIG. 4 schematically depicts (a) a target HIV-1 envelope plasmid (pENVwt); (b) a mutated competitor plasmid (pENVcomp), priming regions 88–79, 88–272, T7 and T3 rev, probe detection regions HE3 and HE5; and (c) a standard construct (pENVwc).
Figure 5A:
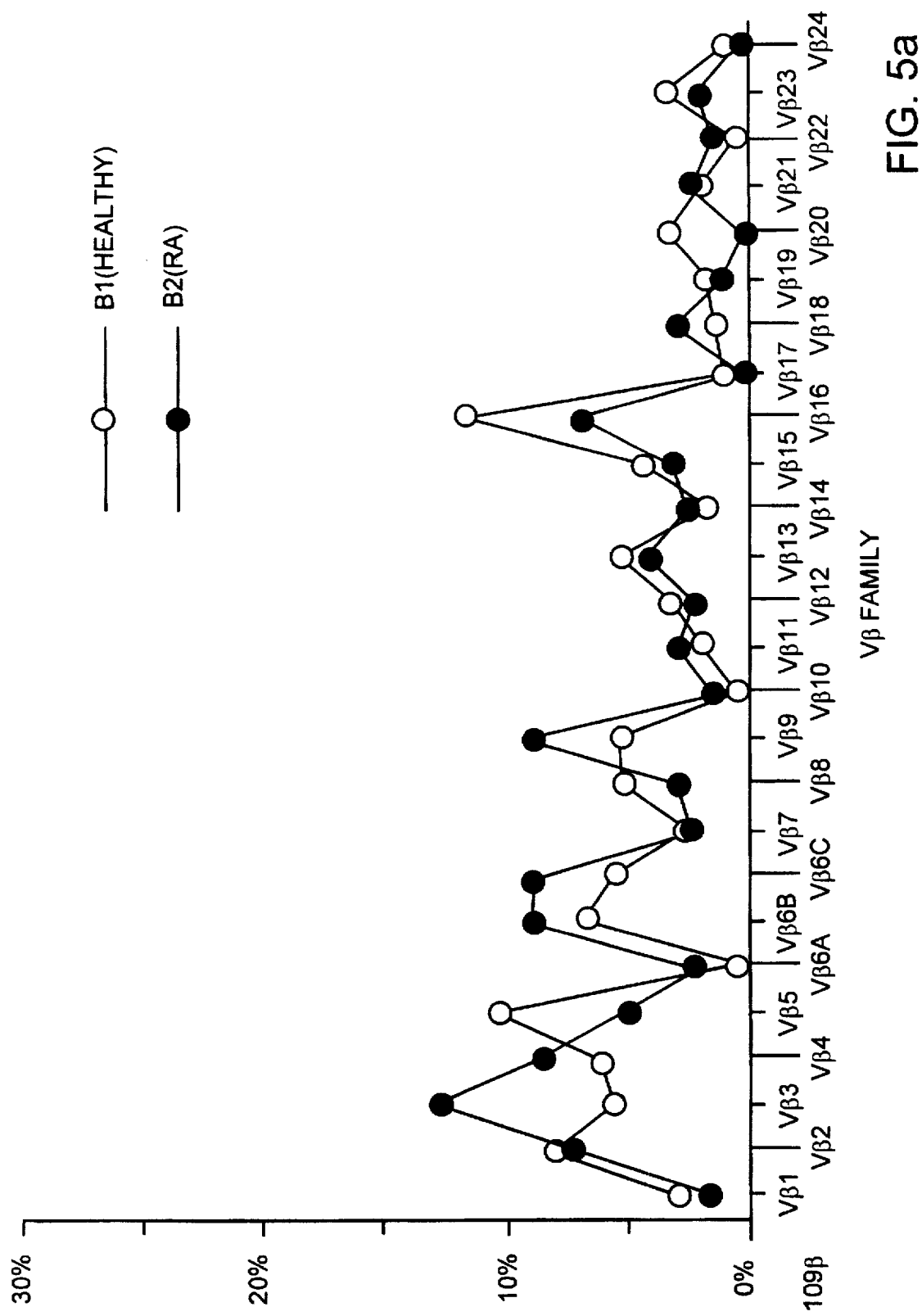
FIG. 5 (a)–(g) depicts the results of an assay performed according to the invention to determine the frequency of a T cell receptor gene in a sample.
Figure 5B:
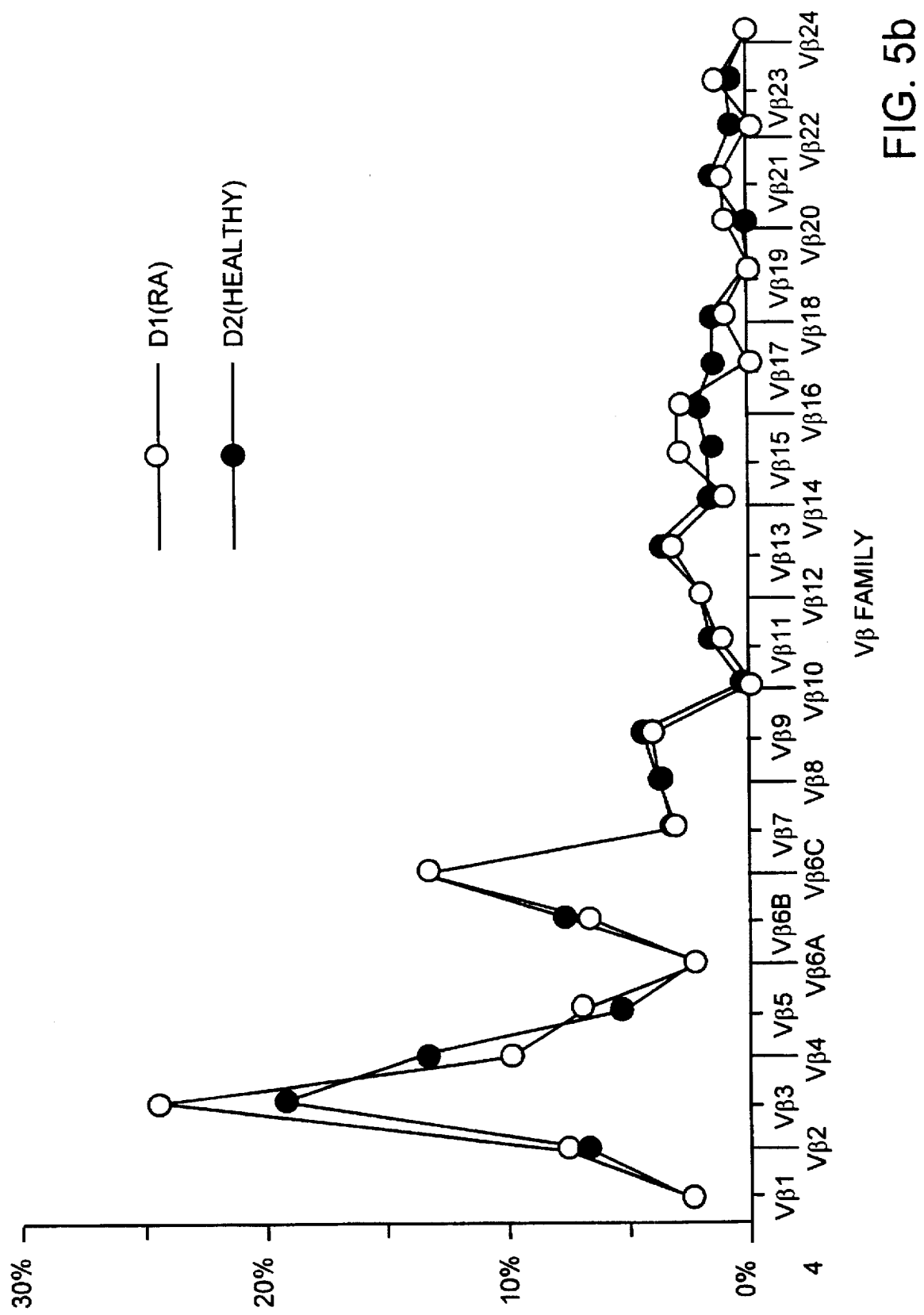
Figure 5C:
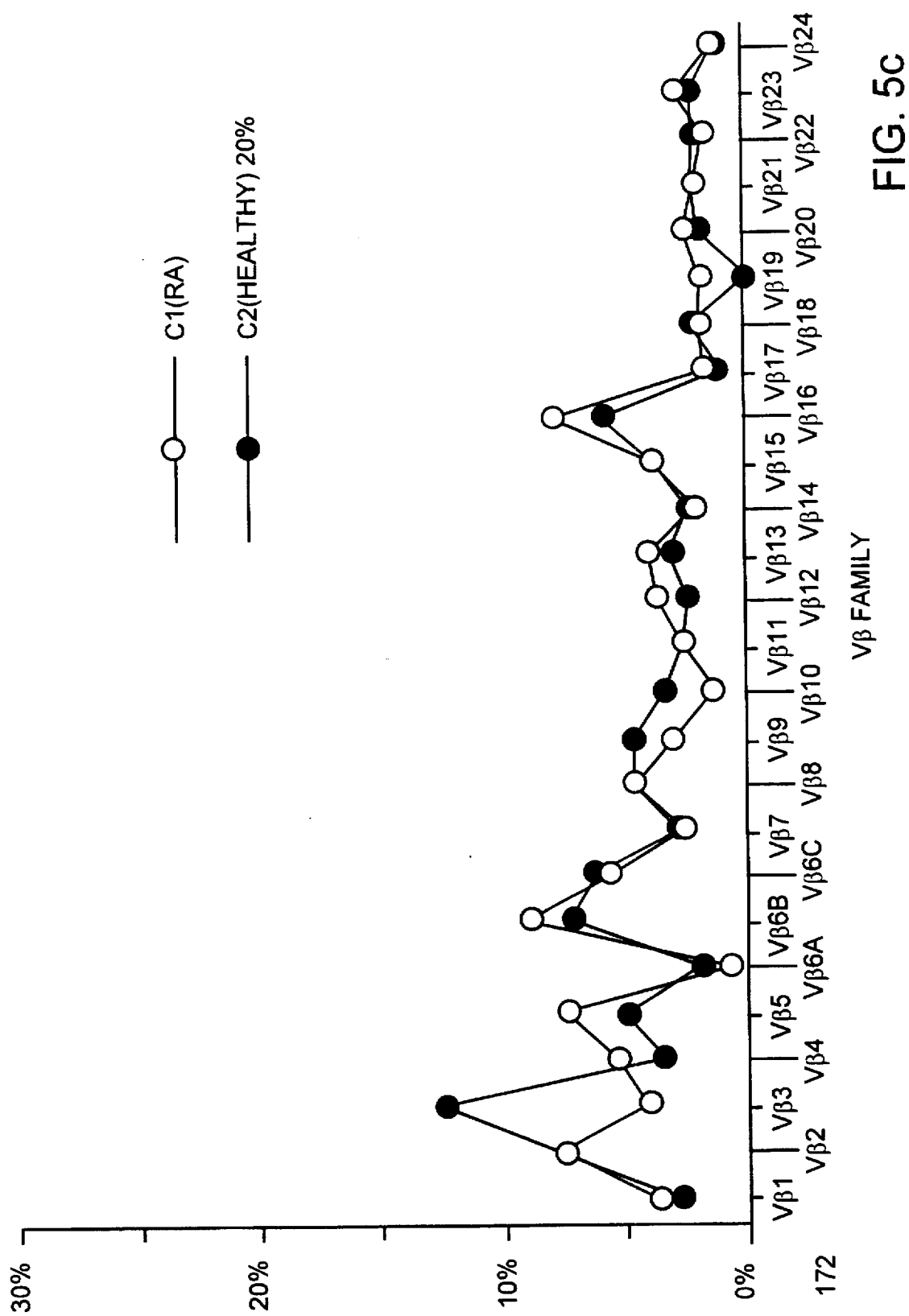
Figure 5D:
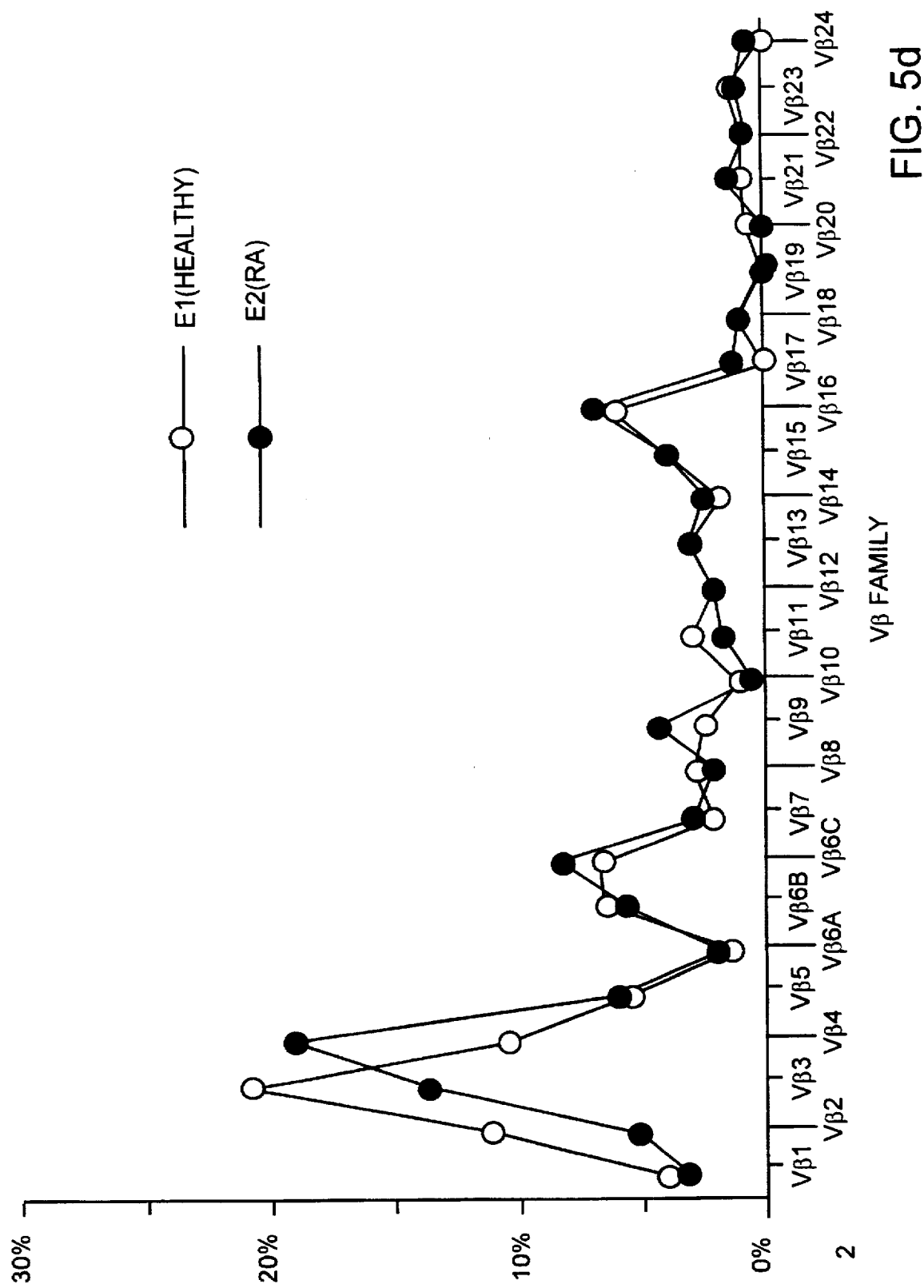
Figure 5E:
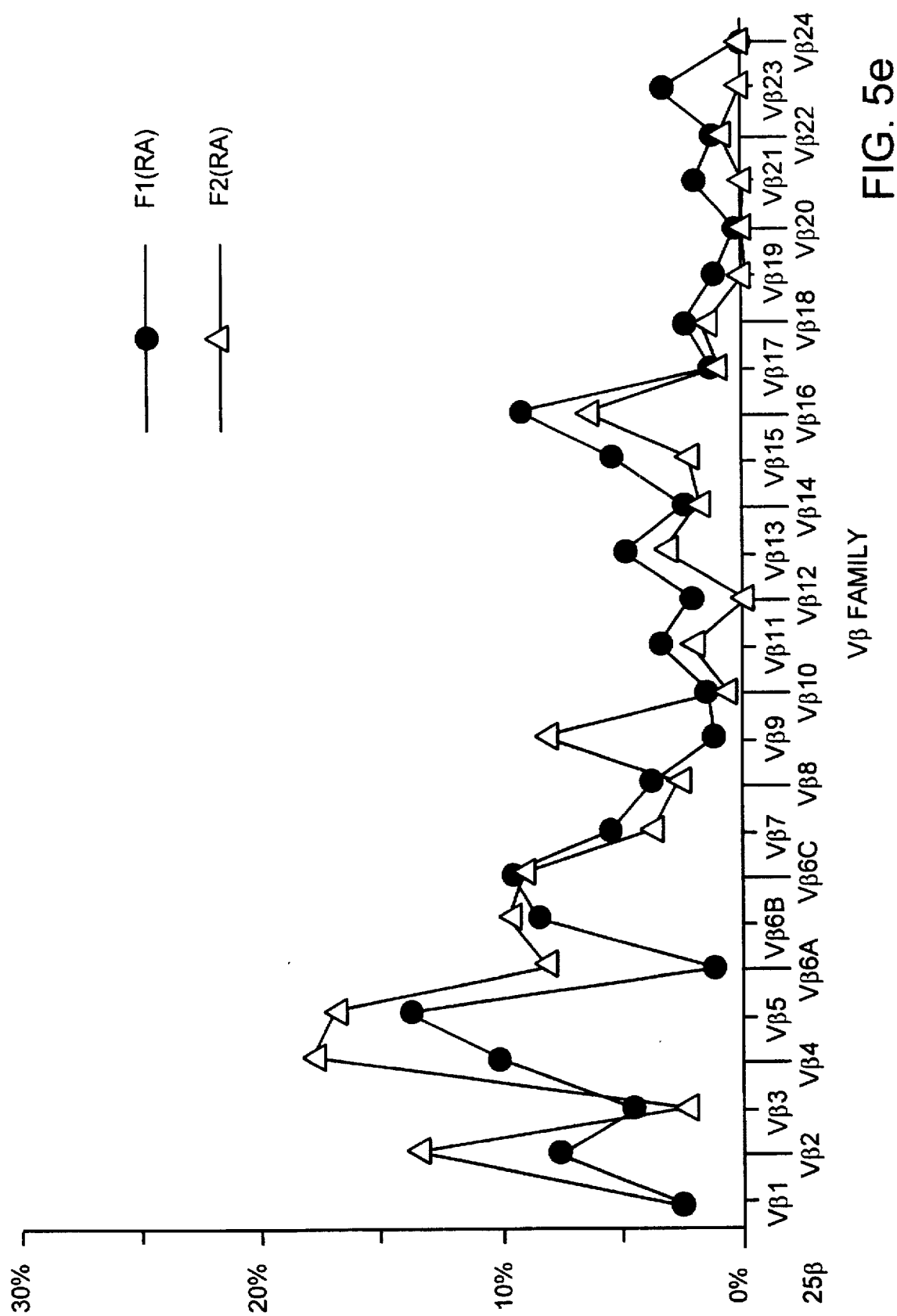
Figure 5F:
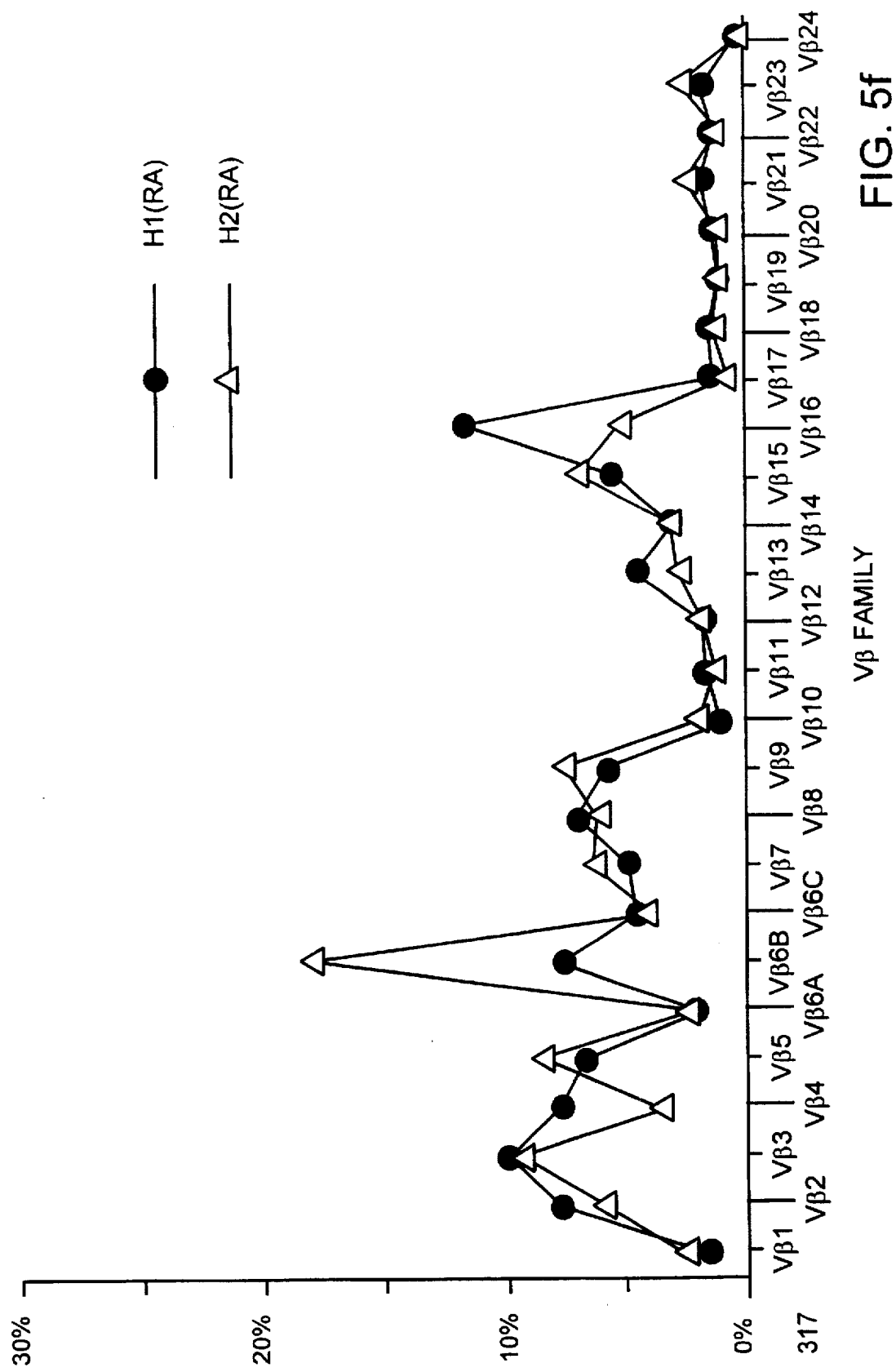
Figure 5G:
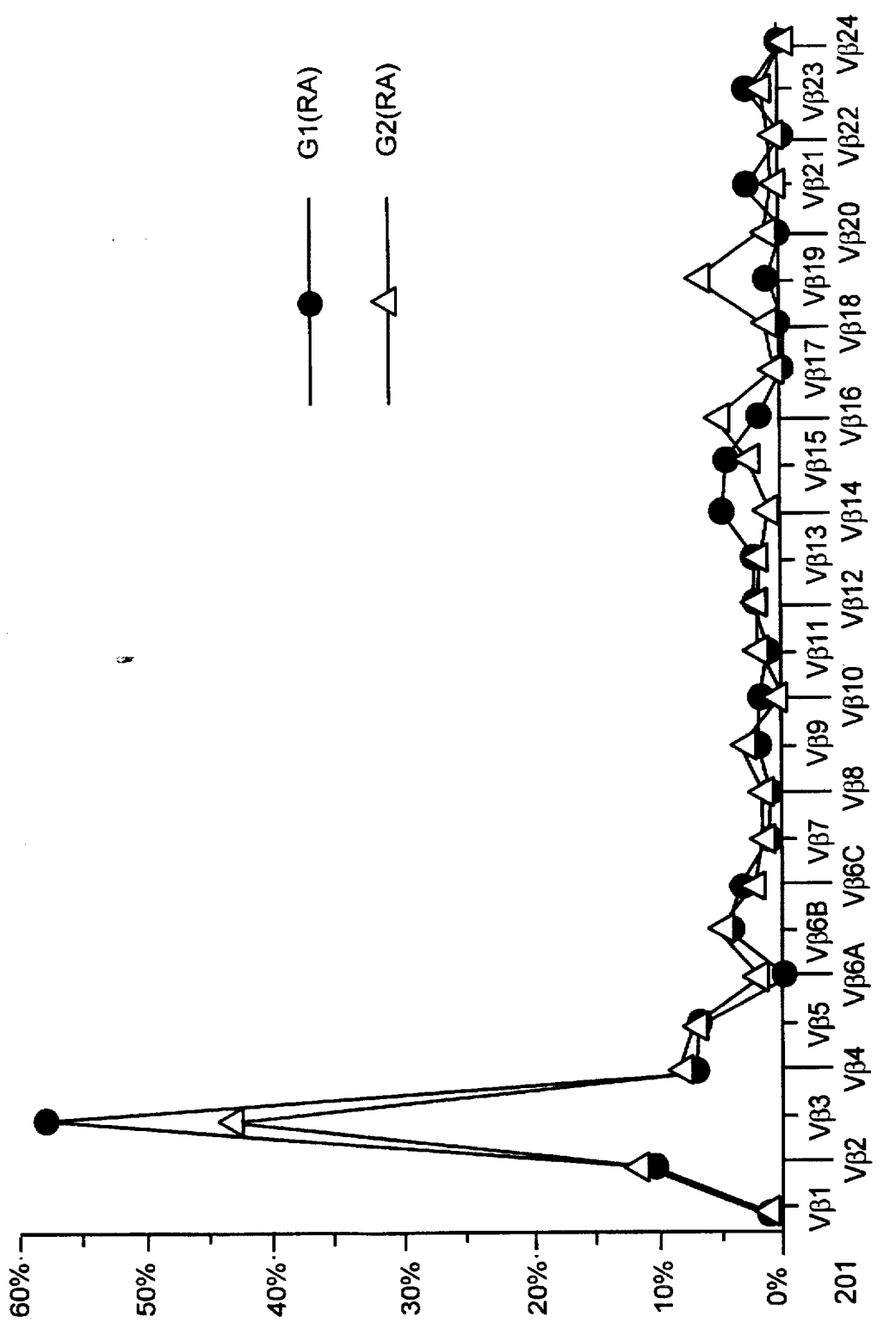

The cloned mutant env gene fragment was isolated from pENVcomp and inserted into pENVwt, to generate a standard plasmid containing tandemly aligned wild type and mutant env genes (pENVwc, depicted in FIG. 4(*c*); "wc"= standard construct)

C. Amplification of Target HIV-1 env Gene with Competitor DNA

One in 10 of the reverse transcribed HIV env gene was mixed with known amounts of mutant competitor plasmid DNA (1 attamol, 100 zeptomol or 10 zeptomol), the insert fragment of which was released from vector with PvuII restriction enzyme digestion. The mixture was subjected to amplification in 100 µl of 10 mM Tris-HCl (pH 8.3), 50 mM KCl, 1.5 mM $MgCl_2$, 0.001% gelatin, 2000 µM dNTPs, 2.5 u Taq DNA polymerase (Boehringer Mannheim) with 88–272 and 5' end aminated 88–79 primers present at a concentration of 1 µM. The amplification consisted of 30 cycles of 95° C. for 30 seconds, 50° C. for 30 seconds, and 72° C. for 1 minute followed by final extension for 7 minutes. Free primers were removed with MAGIC PCR PREPS minicolumns and eluted with 1 mM EDTA (pH 8.0).

D. Amplification of Standard DNA

The tandemly aligned env standard DNA construct and its mutant (the competitor) were amplified from pENVwc using a T3 Rev primer (5'-AAT TAA CCC TCA CTA AAG) (SEQ ID No:3) and an animated T7 primer (5'-primary amine-AAT ACG ACT CAC TAT AG) (SEQ ID No:4). These primers correspond to regions of the pBluescript II plasmid (Stratagene). The amplification consisted of 30 cycles of 95° C. for 30 seconds, 41° C. for 30 seconds and 72° C. for 1 minute followed by final extension of 7 minutes. Free primers were removed as described above. The concentration of the product DNA was determined by direct visualization on agarose gel with ethidium bromide, compared to known DNA standards. This was used to standardize each probe hybridization.

E. Covalent Capture of Amplified DNA and Removal of Sense Strands

20 µl of 8 mg/ml 1-ethyl-3-(3-dimethylaminopropyl) carbodiimide hydrochloride (Pierce of Piscataway, N.J.), 5 mM N-hydroxysulfosuccinamide (Pierce) were placed in each well of 96 well microtiter plates with carboxylated surfaces (Costar). The concentrations of both were chosen to optimize DNA capture onto the plate by application of the discussion in Staros, et al, *Anal. Biochem* (1986) 156:220–222. Immediately, 20 µl aliquots of PCR products diluted in ME buffer (50 mM 2-[N-morpholino] ethanesulfonic acid and 1 mM EDTA, pH 5.5) were added to each of two wells and were incubated at 37° C. for 2 hours. After washing three times with PBS, 100 µl of 0.1N NaOH was placed and left for 10 minutes. Plates were then washed once with 0.1×SSC, and twice with HW buffer (3×SSC, 0.1% N-lauroylsarcosine).

F. Generation of Standard Curve Using a Standard Construct

Figure 6:
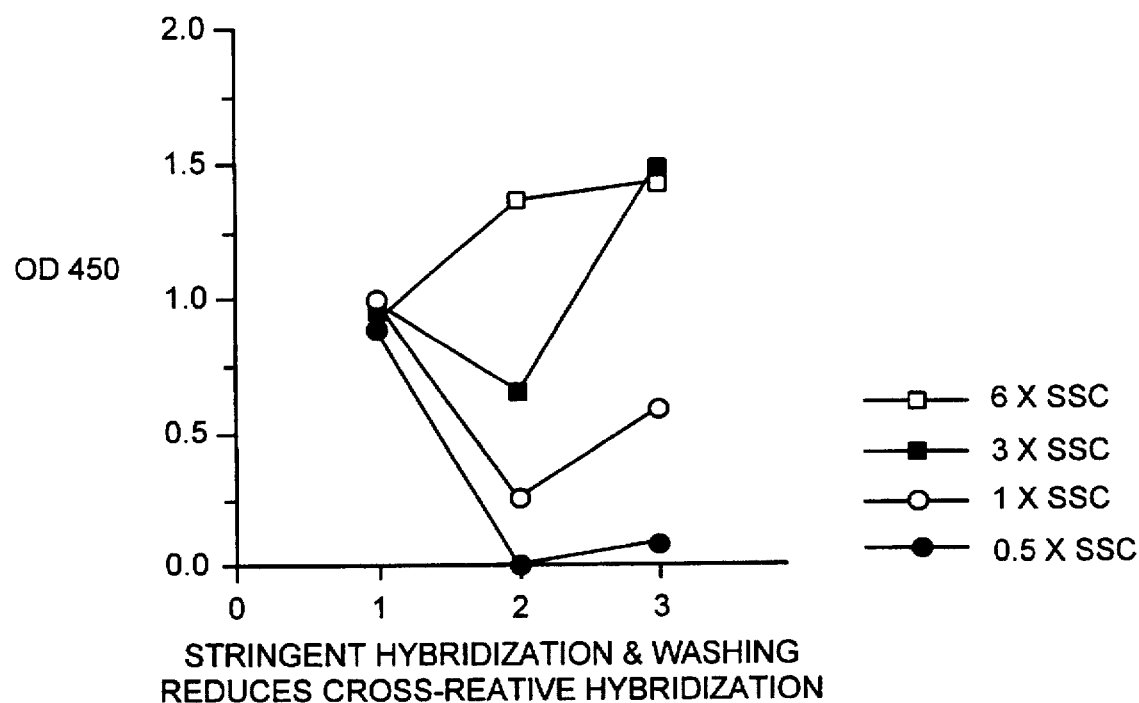
FIG. 6 depicts the results of a genotyping assay for HLA DRB1 genes

One to 100 fmol of the amplified standard constructs were covalently captured as described supra onto wells of a microtiter plate in duplicate. After removal of non-targeted strands with 0.1N NaOH, one set of wells was incubated with digoxigenin-labeled HE3 and the other was incubated with labeled HE5. Hybridized probes were detected with anti-digoxigenin antibody conjugated with peroxidase and chromogen. As shown in FIG. 6, both probes showed a similar hybridization efficiency.

G. Sequence-Specific Oligonucleotide Hybridization

Two oligonucleotides HE3 (5'-CAT TGT ACT GTG CTG AC) (SEQ ID NO:5) and HE5 (5'ACG CCA TTT GAC CAT TC) (SEQ ID NO:6) were synthesized to detect the wild type env gene and the mutant competitor, respectively. They were labeled with a single molecule of digoxigenin-ddUPT (Boehringer Mannheim) using terminal transferase. 5 pmol/ml of labeled oligonucleotide in HW buffer was placed into the well and the plates were incubated at 65° C. for 20 minutes, and then at 42° C. for 90 minutes. After washing three times with HW buffer and once with blocking buffer

[0.5% Genius blocking reagent (Boehringer Mannheim) in 100 mM Tris-HCl (pH 7.5), 800 mM NaCl], they were incubated with 100 µl of 150 mu/ml peroxidase conjugated anti-digoxigenin antibody (Boehringer Mannheim) in blocking buffer for 30 minutes. The wells were washed once with blocking buffer, twice with 100 mM Tris-HCl (pH 7.5), 800 mM NaCl, and incubated with 100 µl of tetramethylbenzidine and peroxidase (Kirkegaard & Perry Laboratories). The reaction was stopped with 1M o-phosphate at the appropriate time point.

Optical densities were measured at 450 nm with a microplate reader (Molecular Devices) and were transformed to concentrations using the DELTA SOFT 2.1 software program (BioMetallics).

H. Quantification of HIV env Genes in HIV-Infected CEM Cells

The amount of competitor DNA added and the ratio of wild type products to mutated products were plotted in a log scale graph. The initial amount of HIV-1 env cDNA was determined by calculating the amount of competitor which would give a 1:1 ratio (see, FIG. 3). Data obtained in three independent amplification were 170, 190, 160 fmol. When triple the amount of the input cDNA was analyzed in the same method, the calculated env gene dose was 480 fmol.

EXAMPLE III

PERFORMANCE OF METHOD OF EXAMPLE I TO DETERMINE FREQUENCY OF EXPRESSION OF A T CELL RECEPTOR GENE IN HUMAN PATIENTS WITH RHEUMATOID ARTHRITIS USING THE METHOD OF EXAMPLE I

Rheumatoid arthritis (RA) is characterized by T lymphocyte infiltration into hyperplastic synovial (joint) tissues. Either genetic or environmental factors could affect RA incidence or severity by altering the T cell repertoire. The analysis of DNA for the presence of particular mutations or polymorphisms can be accomplished to some extent by differential hybridization with sequence-specific probes. Use of the PCR to amplify the quantity of DNA in a sample has simplifies genetic typing for the samples. However, conventional typing techniques can result in a substantial number of false positives because small differences in alleles are not distinguished. The methods of the invention can be adapted to this purpose as generally described below.

The inventive method was used on a noncompetitive basis to analyze expression of 24 different T cell receptor (TCR) gene alleles (differing in the variable region) in peripheral blood lymphocytes from five pairs of monozygotic twins who were discordant for RA, and in three twin pairs who were concordant for RA. Non-parametric statistical analyses of the TCR gene repertoires showed that they are significantly more alike in monozygotic twins that in unrelated subjects. In contrast, there were no significant differences in TCR variable region gene usage in the RA affected twins that could be attributed to the disease alone, independent of genetic variables.

A. Materials

1. Analyzed Lymphocytes. Peripheral blood mononuclear lymphocytes (PBMC) were isolated by density gradient sedimentation from heparinized peripheral blood. Peripheral lymphocytes from a donor were stimulated with three bacterial superantigens. Staphylococcal enterotoxin B (SEB), staphylococcal enterotoxin E (SEE) and toxic shock syndrome toxin-I (TSST-I) were purchased from Toxin Technology of Sarasota, Fla. For the stimulation of cells with superantigens, cells were incubated with 1 mg/ml of superantigens for 72 hours in RPMI 1640 medium (Irvine Scientific, Irvine, Calif.) supplemented with penicillin G (50 µ/ml), streptomycin (50 mg/ml) and L-glutamine (0.3 mg/ml) and 10% heat inactivated human serum from normal AB-positive blood donors. The lymphoblastoid cell lines, Jurkat cells and HBP-AII cells came from the American Type Culture Collection (Rockville, Md.).

2. Oligonucleotides. Oligonucleotides used in this study were synthesized with the Applied Biosystems DNA synthesizer. BTNCβb and BTNCβc biotinylated TCR gene alleles were biotinylated with biotinylated phosphoramadite (purchased from Clontech, Palo Alto, Calif.). Oligonucleotides complementary to Cβ (constant) region genes were designed to specify both Cβ1 and Cβ2 genes. The total number of Vβ (variable) gene family members has reached 24 according to the accumulated reports of Vβ gene sequences; oligonucleotides complementary to 98% of reported sequences were constructed. Based on computer analysis with the Genetics Computer Group sequence analysis software programs, the probe with minimal mismatch with non-targeted TCR Vβ gene is a Vβ12a probe. Theoretical dissociation temperatures of all oligonucleotides range from 64° C. to 78° C. in the hybridization solution.

3. Cross-linking of Streptavidin to ELISA plates. 200 µl of 1 mg/ml Bis (sulfosuccinimidyl) suberate (purchased from Pierce, Rockford, Ill.) in phosphate buffered saline (ph 7.4) (PBS) was placed in the wells of polystyrene plates with aminated surface (Covalent EIA plate, purchased from Costar, Cambridge, Mass.) for 15 min at room temperature. After washing with PBS, the wells were incubated with 200 µl of 0.1 mg/ml streptavidin (Sigma, St. Louis, Mo.) in PBS at 37° C. for 2 hours. The wells were washed with PBS and stored at 4° C. until used. Before the assay, non-covalently bound streptavidin was removed by incubation with 0.1% Triton-X100 for 30 min at room temperature. This step is necessary to avoid removal of the streptavidin during the subsequent alkali denaturation step. Blocking was carried out with 1% bovine serum albumin (BSA) (fraction V, RIA grade, Sigma) for 2 hours at room temperature.

4. Labeling oligonucleotide probes with digoxigenin. The sense oligonucleotide probes specific to V3 family genes were labeled with a single molecule of digoxigenin in 20 µl of 5 µM oligonucleotide, 200 mM potassium cacodylate, 25 Mm Tris-HCl (pH 6.6), 250 mg/ml BSA, 5 Mm $CoCl_2$, 50 µM digoxygenin-dideoxy UTP (Boehringer Mannheim, Indianapolis, Ill.), and 50 µ terminal deoxytransferase. Labeled oligonucleotides were purified by ethanol precipitation. The biotinylated Cβ oligonucleotide, (BTNCβc) was labeled with digoxigenin in the same manner for making standard curve in ELISA.

B. Covalent Capture Competitive PCR using Anchored PCR Followed by Nested PCR Total RNA was isolated from $5 \times 10^5$ PBMC, lymphoblastoid cells or superantigen-stimulated cells using RNAzolB (Cinna/Biotecx, Friendswoods, Tex.), which is based on the acid guanidium thiocyanate-phenol-chloroform method known in the art. First strand cDNA was synthesized from total RNA using an oligo-dT primer and superscript reverse transcriptase (Life Technologies, Gaithersburg, Md.). The resulting cDNA/RNA hybrids were first size selected (0.5–3 kb) on agarose gels and extracted with phenol. The remaining RNA was hydrolyzed by incubation at 60° C. in 0.3M NaOH.

To amplify entire TCRβ V domain cDNA and competitor segments regardless of sequence, anchored PCR is performed. To this end, the first strand cDNA and competitor were poly dG-tailed with dGTP and terminal deoxytransferase. Subsequently, free dGTP was removed by two sequential ammonium acetate precipitation steps. The G-tailed DNA's were subjected to primary anchored PCR amplification in 100 µl of 10 mM Tris-HCl (pH 0.3), 50 mM KCl, 1.5 mM MgCl$_2$, 0.001% gelatin, 200 µM dNTP's, 1 Unit PERFECT MATCH POLYMERASE ENHANCER (from Stratagene of La Jolla, Calif.) and 2.5 Units Taq DNA polymerase (from Boehringer Mannheim). The primers consisted of a Cβ-specific anti-sense oligonucleotide (Cβa) and anchor primers (9:1 mixture of AN primer and ANC primer), at a concentration of 1 µM. The amplification included 15 or 20 cycles of 55° C. for 30 seconds, 42° C. for 30 seconds and 72° C. for 1 minute followed by final extension of 7 minutes.

The products were size selected (500–750 base pairs) on agarose gels and one third were removed for nested PCR. The reaction mixture was the same as that of the primary anchored PCR except for the primers, 1 µM each of AN primer and 5' biotinylated Cβb anti-sense primer were used, the latter of which primes upstream of the Cβa primer sequence. Twenty cycles of nested PCR were carried out at an annealing temperature of 53° C., and the products were purified by minicolumn (MAGIC PCR PREPS, Promega, Madison, Wis.). The nested PCR with BTNCβb primer was not only to increase specificity of amplification, but also to put biotin molecule at the 5' end of the antisense strands of the PCR products.

The PCR products, resuspended in 100 µl of 6×SSC, 0.1% Tween-20, were distributed to 26 streptavidin-bound wells and left for 1 hour at room temperature. After PCR products were captured at the 5' termini of biotinylated antisense strand, sense strands were removed by incubating with 0.1N NaOH for 5 min, and washed once with 0.1×SSC and twice with 6×SSC. 150 µl each of 25 mM labeled oligonucleotide probe in 6×SSC, 0.1% 20 N-lauroylsarcosine was placed in the corresponding wells and the plates were heated at 65° C. for 20 min and incubated for 90 min at 42° C.

C. Enzyme-Linked Immunosorbent Assay

After the wells were washed three times with 6×SSC, once with 0.1% N-lauroylsarcosine and once with blocking buffer (using 0.5% GENIUS blocking reagent from Boehringer Mannheim) in 100 Mm Tris-HCl (pH 7.5) and 800 Mm NaCl suspended in blocking buffer), they were incubated with 100 µl of 150 mu/ml anti-digoxigenin peroxidase (purchased from Boehringer Mannheim) for 30 minutes. The wells were washed once with blocking buffer, twice with 100 mM Tris-HCl (pH 7.5), 800 mM NaCl, and incubated with 100 µl of tetramethylbenzidine and peroxidase (purchased from Kirkegaard & Perry Laboratories, Gaithersburg, Md.). Reaction was stopped with 1M O-phosphate at the appropriate time point and OD in each well was measured at 450 nm.

For generating a standard curve, biotinylated oligonucleotide, BTNCβc was labeled with digoxigenin-ddUTP. Serially diluted different concentrations of oligonucleotide, ranging from 48 amol/100 µl to 100 fmol/100 µl, were applied onto the streptavidin-bound wells and treated like samples except for the NaOH denature. After the assay, the absorbance value of each wells was transformed to the concentration by comparison to the standard curve using the DELTASOFT software program as described supra and the frequency of each Vβ gene transcript was calculated. The results of this assay are shown in FIG. 5 (a)–(g).

EXAMPLE IV

TYPING OF HLA (CLASS II) DRB GENES

The method described in Example III can also be used for HLA genotyping, where allelles can differ by as few as three base pairs. In Marsh, et al., *Tissue Antigens*, (Gene Registry) 37:181–189, 1991, known nucleotide sequences for HLA Class II genes are described and identified using accepted nomenclature. Using these sequences, appropriate primers and SSO's can be selected and labelled as described in the "Arthritis and Rheumatoid Epidemiology Research Unit Manual for Performing Conventional Tissue Typing" published and distributed by the University of Manchester, Manchester, England, United Kingdom. The manual sets forth accepted conventional protocols for HLA DRB genotyping.

Using primers and SSO's selected and prepared according to conventional techniques, appropriate coupling agents and detection tags can be added according to the methods of this invention. The character of each allele present can be determined as taught herein.

For example, using the DRB generic primers:

1: CCC CAC ACG TTT CTT G  (SEQ ID. NO: 7)

and

2  CCC CTG CAC TGT GAA GCT CT  (SEQ ID. NO: 8)

and the digitoxigen (DIG) labelled oligonucleotide probe DRB 7004 (Marsh, et al., supra, genomic DNA drawn from 3 human serum donors was amplified and assayed using the method of Example III herein.

In donor 1, the DRB1/0301 gene was detected. In donor #2, the DRB1/0403 genes were detected. In donor #3, the DRB1/0701 gene was detected. These alleles differ in nucleotide sequence by as few as four base pairs from each other and by as few as four base pairs from the labelled probe (see, Marsh, et al., supra).

Cross-reactive hybridization in this experiment was substantially reduced by stringent denaturing conditions which enhanced removal of sense strands in solution. The results obtained under different hybridization and washing different salt concentrations are shown in FIG. 6; for the most part, more salt obtained more false positives. Therefore, results obtained from each embodiment of this invention can be expected to be enhanced by maintaining stringent hybridization conditions (i.e., limiting the concentrations of salt used in the washing steps along the guidelines suggested by the results shown in FIG. 6).

EXAMPLE V

SOLID PHASE DNA POLYMERIZATION USING A PRIMER TIGHTLY BOUND TO A SOLID PHASE SUPPORT FOLLOWED BY HYBRIDIZATION (ALTERNATIVE METHOD)

This example demonstrates the embodiment of the invention wherein the final two primer polymerization step (if any) and the hybridization step take place on the solid phase support. The method was used to determine the quantity of HIV-1 env gene in a sample.

A. Covalent Capture of Aminated Primer

Primers were chosen as described in Example VIII, supra. The 88–79 primer (AAA GGT ATC CTT TGA GCC AAT TCC CAT AC) (SEQ ID NO:9) was aminated as described in Example I(c), supra.

Aliquots of a solution formed of A 40 µl of 2.5 pmol/µl aminated HIV-1 envelope gene oligonucleotide (designated 88–79; AAA GGT ATC CTT TGA GCC AAT TCC CAT AC) (SEQ ID NO:9), 20 µl of 4 mg/ml 1-ethyl-3-(3-dimethylaminopropyl) carbodiimide hydrochloride (EDC, Pierce), 2.5 mM N-hydroxysulfosuccinumide (Pierce), 25 mM MES and 0.5 mM EDTA (pH 5.5) was placed in each well of 96 well multititer plates with a carboxylated surface (Costar) and incubated at 37° C. for 4 hours. The wells were washed three times with TE buffer.

B. Solid-Phase Polymerization 100 amol of HIV env wild type gene (as described in Example VIII), or the same quantity of a mutated competitor (constructed as described in Example VIII, supra), were coamplified in the plate wells with the precaptured primer. The amplification mixture consisted of 50 µl of 10 mM Tris-HCl (pH 8.3), 50 mM KCl, 1.5 mM MgCl$_2$, 0.001% gelatin, 200 µM of a primer (designated 88–272) (see FIG. 4). The amplification consisted of 40 cycles of 95° C. for 1 minute, 45° C. for 10 minutes, and 72° C. for 1 minute, followed by final extension for 7 minutes.

C. Removal of Unbound Antisense Strands

The plate wells were washed once with PBS and blocked with 1% BSA in PBS for 1 hour. After washing three times with PBS, 100 µl of 0.1N NaOH was added to the wells and left for 10 minutes. Plates were then washed once with 0.1×SSC, and twice with HW buffer (3×SSC 0.1% sarcosyl).

D. Solid Phase Oligonucleotide Hybridization

An oligonucleotide, designated HE3 (CAT TGT ACT GTG CTG AC (SEQ ID NO:5); described in Example VIII) was synthesized to specify the wild type HIV envelope gene. It was labeled with a single molecule of digoxigenin-ddUTP (Boehringer Mannheim) by terminal transferase as suggested in Example 1(d), supra. Ten pmol/ml of labeled oligonucleotide in HW buffer was placed into the well and the plates were incubated at 65° C. for 20–25 minutes, and then at 42° C. for 90 minutes.

After washing three times with HW buffer and once with blocking buffer [0.5% GENIUS blocking reagent (Boehringer Mannheim) in blocking buffer for 30 minutes. Afterward, the wells were washed once with blocking buffer, twice with 100 mM Tris-HCl (pH 7.5), 800 mM NaCl, and incubated with 100 µl of tetramethylbenzidine and horseradish peroxidase (Kirkegaard & Perry Laboratories). The reaction was stopped with 1M o-phosphate at the appropriate time point and OD was measured at 450 nm with a microplate reader (Molecular Devices).

E. Results

The optical density of the well where wild type HIV envelope gene was used as the template was off-scale (≧4.0). The optical density of the well with the mutant competitor template was 0.119 (background value).

EXAMPLE VI

ONE-STEP SOLID PHASE POLYMERIZATION

This example generally demonstrates the steps involved in performing the method of the invention using bound hybridization primers, wherein all of the steps of the assay are performed on a solid phase support. For simplicity, this assay will be performed using a conventional PCR protocol (and one bound hybridization primer) rather than the competitive protocol described previously (which requires the use of 2 bound hybridization primers).

A. Preparation of Templates and Primers

20 µl of 2.5 pmol/µl of the 88–79 oligonucleotide described in Example II was used as a hybridization primer. This primer is specific for HIV-1 envelope gene. The primer was aminated and tightly bound to each well of a 96-well polycarbonate microtiter plate in the presence of 20 µl of 4 mg/ml 1-ethyl-3-(3-dimethyl-animopropyl) carbodiimide hydrochloride CEDC, from Pierce Chemical), 25 mM MES and 0.5 mM EDTA (pH 5.5). This hybridization primer-containing solution was incubated at 35° C. for 2 hours then washed once with phosphate buffer solution (PBS). The reaction was stopped with 1% bovine serum albumin.

B. Heat-Stabilization of Solid Phase Support

As described in Examples I through IV, the plate wells (or other solid phase support) must be able to tightly bind with an appropriate reactant. A preferred material, therefore, is polystyrene plastic. However, untreated polystyrene plastic is not sufficiently stable to the high temperatures needed to perform the PCR step in this embodiment of the invention.

Polystyrene may, however, be chemically modified to be sufficiently heat-stable by chemical modifications known to those skilled in the preparation of plastics. Examples of suitable polystyrene compositions include polymethylstyrene, isotactic polystyrene or dichloropolystyrene. Surprisingly, commercially available polycarbonate plates will also bind with the reactant and are sufficiently heat stable for use in this method. When a polycarbonate plate is used, the preferred thermal cycler for use in performing the polymerase chain reaction is the PTC-100 from M & J Research. The polycarbonate plate supplied by Costar under the tradename THERMOWELL and equivilent plates supplied by M & J Research are suitable for use in this method of the invention.

The identity of other suitable materials will be apparent to those skilled in the art and will be those materials which (a) are capable of forming tight bonds as defined herein and (b) have melting points above the highest temperatures to be reached in the polymerase chain reaction step (usually 95° C.).

C. Multiple Primer PCR

Fifty fmol, 500 amol, 5 amol, 50 zeptomol of HIV ENV wild type (target) gene were subcloned into the pBluescript plasmid (Invitrogen, San Diego, Calif.). 500 amol of the target gene-containing plasmid were amplified using an appropriate conventional primer pair in the primer precaptured wells. The amplification mixture consisted of 40 µl of 10 mM Tris-HCl (pH 8.3), 50 mM KCl, 1.5 mM MgCl$_2$, 0.001% gelatin, 10 mg/ml BSA, 50 µM dATP, 50 µM dCTP, 50 µM dGTP, 33.3 µM dTTP, 16.7 µM digoxigenin-dUTP (Boehringer Mannheim, Indianapolis, Ind.), 10 u Taq DNA polymerase (Boehringer Mannheim), 0.5 µM of a primer (designated "T3R"; AAT TAA CCC TCA CTA AAG) (SEQ ID NO:11) and 0.01 µM of another primer (designated "M13"; GTA AAA CGA CGG CCA GT) (SEQ ID NO:12). The amplification consisted of 40 cycles of 92° C. for 30 sec, 45° C. for 1 minute and 72° C. for 1 minute.

D. Detection of Hybridization of Extension of the Hybridization Primer in Each Well The wells were washed three times with HW buffer and once with blocking buffer [0.5% GENIUS blocking reagent (Boehringer Mannheim) in 100 mM Tris-HCl (pH 7.5), 800 mM NaCl]. The wells were then incubated with 100 µl of 150 mn/ml anti-digoxigenin peroxidase (Boehringer Mannheim) in blocking buffer for 30 min. The wells were then washed once with blocking buffer, twice with 100 mM Tris-HCl (pH 7.5), 800 mM NaCl, and incubated with 80 µl of tetramethylbenzidine and horseradish peroxidase (Kirkegaard & Perry Laboratories). The reaction was stopped with 80 µl of 1M o-phosphate at the appropriate time point. 150 µl from each well was transferred to another microtiter plate and OD was measured at 450 nm with microplate reader (Molecular Devices).

Figure 7:
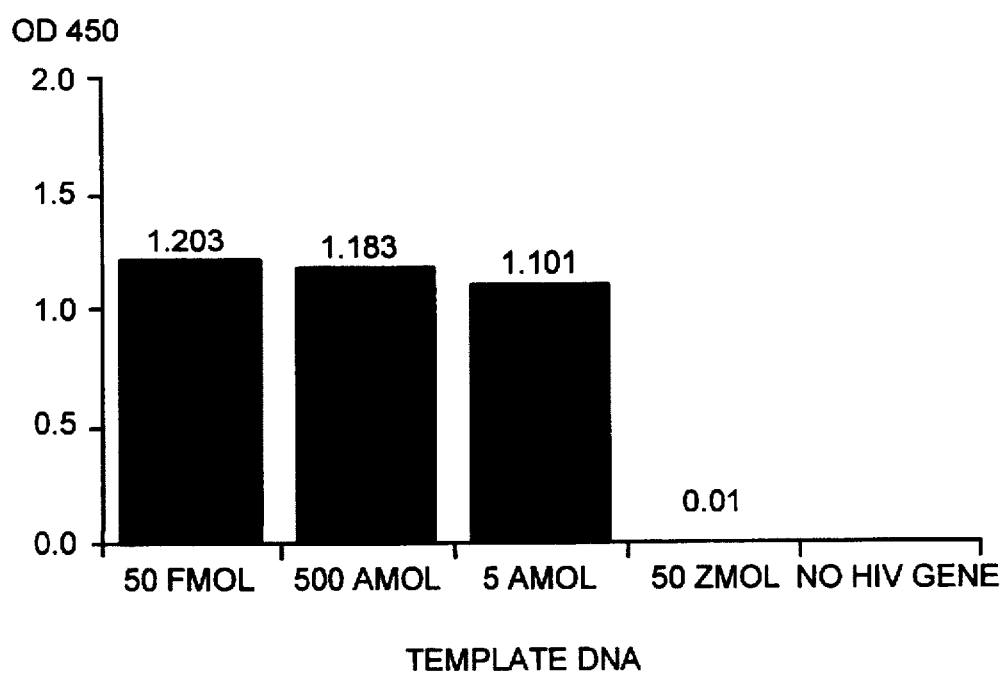
FIG. 7 depicts the results of a one-step assay using a bound hybridization primer and a conventional primer pair corresponding to a target HIV-1 envelope gene.

The optical density measured in each well is shown in FIG. 7. The background OD was 0.116. The control (no HIV gene) pBluescript plasmid was amplified by the T3R and M13 primers but these PCR products were not captured by the hybridization primer because the PCR products did not contain the HIV-1 envelope. These results show that the hybridization primer extends only when it hybridizses to PCR products containing the target gene.

The above protocol can be used for a competitive PCR to quantify the amount of target nucleic acid in a sample. In such a protocol, another hybridization primer corresponding to the competitor nucleic acid would be used.

It will be appreciated by those skilled in the art that this method can be modified by attaching hybridization detection tags, subjecting the PCR product to an alkaline denaturing wash to remove the sense strands, and proceeding with hybridization using SSO's as described in the previous Examples. Doing so would, however, eliminate the principal advantage achieved by this method; i.e., the ability to perform the entire assay in a single step. Therefore, if greater accuracy is needed, use of the alternative embodiments of this invention will be preferred.

It will also be apparent to those skilled in the art that the alternative methods described in Examples I and V could be performed without the hybridization step. However, because that would sacrifice the improved accuracy of those methods vis-a-vis prior art methods, elimination of the hybridization step in those embodiments is not recommended.

EXAMPLE VII

PREPARATION OF MICROTITER PLATES HAVING COVALENTLY BOUND STREPTAVIDIN

200 µl of 1 mg/ml Bis (sulfosuccinimidyl) suberate in PBS (ph 7.4) was placed into each well of a commercially available 96 well microtiter plate of polystyrene with an aminated surface. The plates were then allowed to stand for 15 minutes at room temperature, then decanted and washed once with PBS.

200 µl of 0.1 mg/ml streptavidin in a PBS solution was added to each of the wells and allowed to stand at 37° C. for 2 hours. Each well was then washed three times with PBS. A blocking solution (300 µl of BSA in bicarbonate buffer ph 9.4]) was added to each well and allowed to stand at room temperature for 2 hours. Each well was then washed with PBS which was replaced with 0.01% NaN$_3$ in PBS to store the plates.

EXAMPLE VIII

PREPARATION OF CARBOXYLATED MICROTITER PLATES

As an alternative to the method described in Example I, carboxylated microtiter plates for binding with aminated PCR products can be prepared by means known in the art.

Two methods for the addition of carboxyl groups to polystyrene are known in the field of plastics science. One uses high-level gamma radiation of the plates, followed by reaction with an aromatic acid, such as benzoic acid or salicylic acid. The other method requires nitration of the plates with nitric acid, followed by reduction to a free amino group, and coupling to a suitably reactive anhydride of a carboxylic acid, such as succinic anhydride. Carboxylated microtiter plates of polystyrene are also available commercially from Costar of Cambridge, Mass.

EXAMPLE IX

PREPARATION OF AMINATED MICROTITER PLATES

As an alternative to the method described in Examples VII and VIII, aminated microtiter plates can be purchased from Costar.

EXAMPLE X

SSO HYBRIDIZATION WITH AMINATED ANTISENSE STRANDS

The protocol described in Example I can be modified for use of aminated primers as follows. Following the process outlined above, antisense strands are captured onto ELISA plate wells. Sense strands are then removed from the wells and SSO hybridization performed as described below.

Sense strands of the PCR products were removed as follows. 200 µl of 0.1N NaOH was added to each well and allowed to stand for 10 minutes at 37° C. Each well was then washed once with 380 µl of 0.1N NaOH and then twice with 300 µl of BW buffer (6×SSC, 0.1% sarcosyl).

150 µl of each probe (e.g., 10 pmol/ml biotin-labelled probe in 6×SSC, 0.1% sarcosyl) was added to each well. Each well was then heated to 65° C. for 20 minutes and incubated 90 minutes at 42° C. The wells were washed after incubation three times with 6×SSC, 0.1% sarcosyl and again with 380 µl of 0.1% TWEEN-20 in PBS.

100 µl of an appropriate detection reagent (e.g., 2 mg/ml streptavidin-conjugated peroxidase suspended in 0.1% TWEEN-20) was placed in each well and incubated at room temperature for 1 hour. Each well was washed with 380 µl of 0.1% TWEEN-20 once then twice with 380 µl of PBS. 100 µl of tetramethylbenzindine and peroxidase/H707 was placed in each well and the reaction was stopped with 100 µl of 1M o-phosphate.

EXAMPLE XI

COVALENT CAPTURE OF BIOTINYLATED ANTISENSE PCR PRODUCTS AND HYBRIDIZATION

The protocol described in Example I was modified by use of biotinylated primers and microtiter plates having streptavidin covalently bound thereto as follows. 100 µl of the PCR products were placed into each well of a 96 well microtiter plate prepared according to Example I after each well was washed with BW buffer (6×SSC, 0.1% TWEEN-20). The PCR products were suspended in BW buffer and incubated for 1 hour at room temperature. Each well was then washed with 200 µl of BW buffer.

Removal of the sense strands of the PCR products was performed as described above in Example V. 150 µl of probes labelled with DIG-ddUTP suspended in 6×SSC, 0.1% sarcosyl were added to each well, heated to 65° C. and incubated for 90 minutes.

DIG-labelled oligonucleotide probes were prepared by adding 1 molecule of DIG-ddUTP to the 3' end of the oligonucleotide in 20 μl of 5 μM oligonucleotide, 0.2M potassium cacodylate, 25 Mm Tris-HCL (ph 6.6), 0.25 mg/ml BSA., 5 Mm CoCl$_2$, 50 mM DIG-ddUTP, and 50 μ terminal transferase incubated at 37° C. for 15 minutes.

After incubation of the probe in the wells for 90 minutes, the wells were washed three times with 380 μl of 6×SSC, 0.1% sarcosyl and once with blocking buffer B (0.15% casein fraction from non-fat dry milk, 100 mM Tris-HCl [pH 7.5], 800 mM NaCl). 100 μl of 150 mu/ml anti-DIG antibody conjugated with peroxidase in B was placed in each well and incubated at room temperature for 30–90 minutes.

The wells were then washed once with buffer A (100 mM Tris-HCl [pH 7.5], 300 mm NaCl) and twice with buffer B. 100 μl of TMP/H$_2$O$_2$ was placed in each well, then the reaction was stopped with 100 μl of 1M o-phosphate.

While specific embodiments are described herein, it will be understood that the invention is defined by the claims appended hereto, and that embodiments may be within their scope and spirit other than those specifically described. In particular, it will be understood by those skilled in the art that although the steps of the claimed methods are by necessity presented in a particular order, modifications to that order may be made without departing from the scope of the invention.

SUMMARY OF SEQUENCES

SEQ ID NO:1 is the HE1 primer.
SEQ ID NO:2 is the HE2 primer.
SEQ ID NO:3 is the T3 Rev primer.
SEQ ID NO:4 is the T7 primer.
SEQ ID NO:5 is the HE3 primer.
SEQ ID NO:6 is the HE5 primer.
SEQ ID NO:7 is a DRB generic primer.
SEQ ID NO:8 is a DRB generic primer.
SEQ ID NO:9 is the primer 88–79.
SEQ ID NO:11 is the primer T3R.
SEQ ID NO:12 is the primer M13.

We claim:

1. A method for determining the concentration of at least one target nucleic acid from a sample known to contain or suspected of containing the target nucleic acid, which method comprises:

(a) selecting a competitor nucleic acid of the same length as the target nucleic acid which varies in sequence from the target nucleic acid by the presence of one or more adjacent nucleotides not found in the target nucleic acid;

(b) selecting at least two primers for use in amplification of the target nucleic acid and the competitor nucleic acid and modifying one primer by attaching a coupling agent to the 5' end thereof;

(c) coamplifying a known quantity of the competitor nucleic acid with any target nucleic acid present in the sample in an appropriate polymerase chain reaction protocol using the selected primers so that the resulting polymerase chain reaction products will consist of a binding strand having the coupling agent attached thereto and a complementary strand without a coupling agent attached thereto;

(d) placing aliquots of the polymerase chain reaction products onto a solid phase support to which a reactant is tightly bound, wherein the reactant is capable of forming tight bonds with the coupling agent attached to the binding strands and with the solid phase support to form a bridge between the coupling agent and solid phase support, wherein each tight bond is stable under denaturing alkaline conditions;

(e) causing binding to occur between the coupling agent and the reactant, thus immobilizing the binding strands onto the solid phase support;

(f) separating the complementary strands of the polymerase chain reaction products from the immobilized binding strands and removing substantially all of the complementary strands from the aliquots with an alkaline denaturing wash;

(g) placing a sequence-specific hybridization probe complementary to said target nucleic acid and another sequence-specific probe complementary to at least the region of the competitor nucleic acid which varies in sequence from the target nucleic acid, both of which probes have different hybridization detection tags attached thereto, into the diluted aliquots under hybridizing conditions to form nucleic acid/probe hybrids;

(h) adding a reagent capable of interacting with the hybridization detection tag to the aliquots to generate a measurable signal and measuring the signal to determine the concentration of nucleic acid/probe hybrids therein; and (i) calculating the concentration of any of the target nucleic acid present in the sample.

2. A method according to claim 1 wherein the competitor nucleic acid varies in sequence from said target nucleic acid by the presence of three or more nucleotides not found in the target nucleic acid.

3. A method according to claim 1 wherein the coupling agent is selected from the group consisting of an amino group, a carboxyl group, a thiol group and biotin.

4. A method according to claim 1 wherein the reactant is selected from the group consisting of an amino group, a carboxyl group, cysteamine and streptavidin.

5. A method according to claim 1 wherein the tight bond is a covalent one.

6. A method according to claim 1 wherein the hybridization detection tag is selected from the group consisting of enzymes, antigens, fluorescent molecules, chemiluminescent molecules, bioluminescent molecules and colloidal metals.

7. A method according to claim 1 wherein the measurement of the concentration of nucleic acid/hybrid probes is determined by an enzyme-linked immunosorbent assay.

8. A method according to claim 1 wherein the solid phase support comprises microtiter plate wells, glass fibers or beads formed of a material which is capable of forming tight bonds with the reactant which are stable under denaturing alkaline conditions and is selected from the group consisting of glass, plastics, polysaccharides and nylons.

9. A method for determining the concentration of a target nucleic acid from a sample known to contain or suspected of containing the target nucleic acid, which method comprises:

(a) selecting a competitor nucleic acid of the same length as the target nucleic acid which varies in sequence from the target nucleic acid by the presence of one or more adjacent nucleotides not found in the target nucleic acid;

(b) selecting at least two primers for use in amplification of the target nucleic acid and the competitor nucleic acid and modifying one primer to attach a coupling agent to the 5' end thereof;

(c) causing the coupling agent to form a tight bond with a reactant which is tightly bound to a solid phase support to immobilize the primer attached to the coupling agent onto the solid phase support, wherein the bonds are stable under denaturing alkaline conditions;

(d) contacting aliquots of a known quantity of the competitor nucleic acid and the sample with the solid phase support and hybridizing the competitor and target nucleic acids with the immobilized primer and extending the primer by polymerization to form polymerization products;

(e) separating the complementary strands of the polymerization products from the immobilized binding strands and removing substantially all of the complementary strands from the aliquots with an alkaline denaturing wash;

(f) placing a sequence-specific hybridization probe complementary to said target nucleic acid and another sequence-specific probe complementary to at least the region of the competitor nucleic acid which varies in sequence from the target nucleic acid, both of which probes have a hybridization detection tag attached thereto, into the aliquots under hybridizing conditions to form nucleic acid/probe hybrids;

(g) adding a reagent capable of reacting with the hybridization detection tag to the aliquots to generate a detectable signal and measuring the signal to determine the concentration of nucleic acid/probe hybrids therein; and (h) calculating the concentration of target nucleic acid present in the sample.

10. A method according to claim 9 wherein a known quantity of the competitor nucleic acid is coamplified with any target nucleic acid present in the sample using a polymerase chain reaction protocol performed in a separate reaction chamber prior to hybridization with the immobilized primer.

11. A method according to claim 9 wherein the competitor nucleic acid varies in sequence from said target nucleic acid by the presence of three or more nucleotides not present in the target nucleic acid.

12. A method according to claim 9 wherein the coupling agent is selected from the group consisting of an amino group, a carboxyl group, a thiol group and biotin.

13. A method according to claim 9 wherein the reactant is selected from the group consisting of an amino group, a carboxyl group, cysteamine and streptavidin.

14. A method according to claim 9 wherein the tight bond is a covalent one.

15. A method according to claim 9 wherein the hybridization detection tag is selected from the group consisting of enzymes, antigens, fluorescent molecules, chemiluminescent molecules, and colloidal metals.

16. A method according to claim 9 wherein the concentration of nucleic acid/probe hybrids is determined by an enzyme-linked immunosorbent assay.

17. A method according to claim 9 wherein the solid phase support comprises microtiter plate wells, glass fibers or beads formed of a material which is capable of forming a tight bond with the reactant and is selected from the group consisting of glass, plastics, polysaccharides and nylons.

18. A kit for use in determining the concentration of a target nucleic acid from a sample known to contain or suspected of containing the target nucleic acid, which kit comprises:

(a) at least one competitor nucleic acid of the same length as, but varying in sequence from, the target nucleic acid by the presence of one or more adjacent nucleotides not found in the target nucleic acid;

(b) primers for use in amplification of the target and competitor nucleic acids, wherein one primer is modified by attachment of a coupling agent to the 5' end thereof;

(c) at least two sequence-specific oligonucleotide probes, one of which is complementary to said target nucleic acid and the other of which is complementary to at least the portion of the competitor nucleic acid which varies in sequence from the target nucleic acid, both of which probes have a hybridization detection tag attached to the 3' end thereof; and, (d) a solid phase support having a reactant tightly bound thereto, which reactant is further tightly bound to the coupling agent on one of the primers, thus immobilizing the primer and coupling agent on the solid phase support, wherein the bonds are stable under denaturing alkaline conditions.

19. A kit according to claim 18 further comprising appropriate reagents for reaction with the hybridization detection tag to form a detectable signal indicative of binding of the oligonucleotide probes to the target or competitor nucleic acid.

20. A kit according to claim 18 wherein the solid phase support comprises microtiter plate wells, glass fibers or beads formed of a material which is capable of forming a tight bond with the reactant which is stable under alkaline denaturing conditions and is selected from the group consisting of glass, plastics, polysaccharides and nylons.

21. A method for determining the presence of a target nucleic acid in a sample suspected of containing said target nucleic acid, which method comprises:

(a) selecting at least two primers for use in amplification of the target nucleic acid by a polymerase chain reaction protocol;

(b) further selecting a hybridization primer which will specifically hybridize to an internal region of the target nucleic acid and modifying the hybridization primer by attaching a coupling agent to its 5' end and a hybridization detection tag to its 3' end of the primer;

(c) causing the coupling agent to form a tight bond with a reactant coating a solid phase support to immobilize the hybridization primer attached to the coupling agent onto the solid phase support, wherein the solid phase support is capable of withstanding temperatures required by the polymerase chain reaction, wherein further the bonds are stable under denaturing alkaline conditions;

(d) amplifying any target nucleic acid present in the sample in the polymerase chain reaction protocol performed on the solid phase support;

(e) adding an effective amount of a reagent capable of interacting with the hybridization detection tag to produce a measurable signal indicative of the formation of nucleic acid hybridization primer hybrids; and, (f) measuring target nucleic acid in the sample.

22. A method according to claim 21 wherein the signal is provided by at least two nucleotide chromophores.

23. A method according to claim 20 wherein the coupling agent is selected from the group consisting of an amino group, a carboxyl group, a thiol group and biotin.

24. A method according to claim 21 wherein the reactant is selected from the group consisting of an amino group, a carboxyl group, cysteamine and streptavidin.

25. A method according to claim 21 wherein the tight bond is a covalent one.

26. A method according to claim 21 wherein the solid phase support comprises microtiter plate readers, glass fibers or beads formed of a material which is capable of forming a tight bond with the reactant and is selected from the group consisting of glass, plastics, polysaccharides and nylon.

27. A method for detecting the presence of at least one target nucleic acid derived from a sample known to contain or suspected of containing the target nucleic acid, which method comprises:

(a) selecting at least two primers for use in amplification of the target nucleic acid and modifying a primer to attach a coupling agent to the 5' end thereof;

(b) causing the coupling agent to form a tight bond with a reactant which is tightly bound to a solid phase support to immobilize the primer attached to the coupling agent onto the solid phase support, wherein the bonds are stable under denaturing alkaline conditions;

(c) contacting aliquots of the sample with the solid phase support and hybridizing the competitor and target nucleic acids with the immobilized primer, then extending the primer by polymerization to form polymerization products;

(d) separating the complementary strands of the polymerization products from the immobilized binding strands and removing substantially all of the complementary strands from the aliquots with an alkaline denaturing wash;

(e) placing a sequence-specific hybridization probe complementary to said target nucleic acid having a hybridization detection tag attached thereto, into the aliquots under hybridizing conditions to form nucleic acid/probe hybrids;

(f) adding an effective amount of a reagent capable of interacting with the hybridization detection tag to the aliquots to generate a measurable signal indicative of the formation of nucleic acid/probe hybrids; and (g) measuring target nucleic acid present in the sample.

28. A method for detecting the presence of a target nucleic acid derived from a sample known to contain or suspected of containing the target nucleic acid, which method comprises:

(a) selecting at least two primers for use in amplification of the target nucleic acid and modifying a primer to attach a coupling agent to the 5' end thereof;

(b) amplifying any target nucleic acid present in the sample in an appropriate polymerase chain reaction protocol using the selected primers so that the resulting polymerase chain reaction products will consist of a binding strand having the coupling agent attached thereto and a complementary strand without a coupling agent attached thereto;

(c) contacting aliquots of the polymerase chain reaction products with a solid phase support to which a reactant is tightly bound, wherein the reactant is capable of forming tight bonds with the coupling agent attached to the binding strands and with the solid phase support to form a bridge between the coupling agent and solid phase support, and wherein the bonds are stable under denaturing alkaline conditions;

(d) causing binding to occur between the coupling agent and the reactant, thus immobilizing the binding strands onto the solid phase support;

(e) separating the complementary strands of the polymerase chain reaction products from the immobilized binding strands and removing substantially all of the complementary strands from the aliquots with an alkaline denaturing wash;

(f) placing a sequence-specific hybridization probe complementary to said target nucleic acid having a hybridization detection tag attached thereto, into the aliquots under hybridizing conditions to form nucleic acid/probe hybrids;

(g) adding an effective amount of a reagent capable of interacting with the hybridization detection tag to the aliquots to generate a measurable signal indicative of the formation of nucleic acid/probe hybrids; and (h) measuring target nucleic acid present in the sample.

29. A method according to claim 9 wherein the polymerization is performed by the polymerase chain reaction and the solid phase support is capable of withstanding temperatures required by the polymerase chain reaction.

30. A kit for use in determining the concentration of a target nucleic acid from a sample known to contain or suspected of containing the target nucleic acid, wherein said kit comprises:

(a) at least one competitor nucleic acid of the same length as, but varying in sequence from, the target nucleic acid by the presence of one or more nucleotides not found in the target nucleic acid;

(b) primers for use in amplification of the target and competitor nucleic acids, wherein one primer is modified by attachment of a coupling agent to the 5' end thereof;

(c) at least two sequence-specific oligonucleotide probes, one of which is complementary to said target nucleic acid and the other of which is complementary to at least the portion of the competitor nucleic acid which varies in sequence from the target nucleic acid, both of which probes have a hybridization detection tag attached to the 3' end thereof; and (d) a solid phase support having a reactant tightly bound thereto, which reactant is capable of forming a tight bond with the coupling agent, wherein each bond is stable under denaturing alkaline conditions.

31. A kit according to claim 30 further comprising appropriate reagents for reaction with the hybridization detection tag to form a detectable signal indicative of binding of the oligonucleotide probes to the target or competitor nucleic acids.

32. A kit according to claim 30 wherein the solid phase support comprises microtiter plates, glass fibers or beads formed of a material which is capable of binding the reactant and is selected from the group consisting of glass, plastics, polysaccharides and nylons.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..30

( x i ) SEQUENCE DESCRIPTION: SEQ ID NO:1:

CGCCATTTGA CCATTCATTT GTACATGGTC      30

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..31

( x i ) SEQUENCE DESCRIPTION: SEQ ID NO:2:

AATGGTCAAA TGGCGTTACA CATGGAATTA G      31

( 2 ) INFORMATION FOR SEQ ID NO:3:

( i ) SEQUENCE CHARACTERISTICS:
        ( A ) LENGTH: 18 base pairs
        ( B ) TYPE: nucleic acid ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO:3:

AATTAACCCT CACTAAAG                                                                                        18

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:4:

AATACGACTC ACTATAG                                                                                         17

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..16

( x i ) SEQUENCE DESCRIPTION: SEQ ID NO:5:

CATTGTACTG TCTGAC                                                                                          16

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..17

( x i ) SEQUENCE DESCRIPTION: SEQ ID NO:6:

ACGCCATTTG ACCATTC                                                                                         17

( 2 ) INFORMATION FOR SEQ ID NO:7:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

```
       ( i x ) FEATURE:
               ( A ) NAME/KEY: CDS
               ( B ) LOCATION: 1..16

( x i ) SEQUENCE DESCRIPTION: SEQ ID NO:7:

CCCCACACGT TTCTTG                                                                      16

( 2 ) INFORMATION FOR SEQ ID NO:8:

( i ) SEQUENCE CHARACTERISTICS:
               ( A ) LENGTH: 20 base pairs
               ( B ) TYPE: nucleic acid
               ( C ) STRANDEDNESS: single
               ( D ) TOPOLOGY: linear ( i i ) MOLECULE TYPE: DNA (genomic)

( i x ) FEATURE:
               ( A ) NAME/KEY: CDS
               ( B ) LOCATION: 1..20

( x i ) SEQUENCE DESCRIPTION: SEQ ID NO:8:

CCCCTGCACT GTGAAGCTCT                                                                  20

( 2 ) INFORMATION FOR SEQ ID NO:9:

( i ) SEQUENCE CHARACTERISTICS:
               ( A ) LENGTH: 29 base pairs
               ( B ) TYPE: nucleic acid
               ( C ) STRANDEDNESS: single
               ( D ) TOPOLOGY: linear ( i i ) MOLECULE TYPE: DNA (genomic)

( i x ) FEATURE:
               ( A ) NAME/KEY: CDS
               ( B ) LOCATION: 1..29

( x i ) SEQUENCE DESCRIPTION: SEQ ID NO:9:

AAAGGTATCC TTTGAGCCAA TTCCCATAC                                                        29

( 2 ) INFORMATION FOR SEQ ID NO:10:

( i ) SEQUENCE CHARACTERISTICS:
               ( A ) LENGTH: 29 base pairs
               ( B ) TYPE: nucleic acid
               ( C ) STRANDEDNESS: single
               ( D ) TOPOLOGY: linear ( i i ) MOLECULE TYPE: DNA (genomic)

( i x ) FEATURE:
               ( A ) NAME/KEY: CDS
               ( B ) LOCATION: 1..29

( x i ) SEQUENCE DESCRIPTION: SEQ ID NO:10:

AAAGGTATCC TTTGAGCCAA TTCCCATAC                                                        29

( 2 ) INFORMATION FOR SEQ ID NO:11:

( i ) SEQUENCE CHARACTERISTICS:
               ( A ) LENGTH: 18 base pairs
               ( B ) TYPE: nucleic acid
               ( C ) STRANDEDNESS: single
               ( D ) TOPOLOGY: linear ( i i ) MOLECULE TYPE: DNA (genomic)

( i x ) FEATURE:
               ( A ) NAME/KEY: CDS
               ( B ) LOCATION: 1..18
```

(x i) SEQUENCE DESCRIPTION: SEQ ID NO:11:

AATTAACCCT CACTAAAG                                                         18

(2) INFORMATION FOR SEQ ID NO:12:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..17

(xi) SEQUENCE DESCRIPTION: SEQ ID NO:12:

GTAAACGAC GGCCAGT                                                           17